(12) United States Patent
Diamandis et al.

(10) Patent No.: US 8,574,860 B2
(45) Date of Patent: Nov. 5, 2013

(54) BIOMARKERS FOR THE DETECTION AND SCREENING OF DOWN SYNDROME

(75) Inventors: Eleftherios P. Diamandis, Toronto (CA); Chan-Kyung Jane Cho, Toronto (CA); Eduardo Martinez Morillo, Toronto (CA)

(73) Assignee: University Health Network, Tornoto (CA)

( * ) Notice: Subject to any disclaimer, the term of this patent is extended or adjusted under 35 U.S.C. 154(b) by 0 days.

(21) Appl. No.: 13/467,661

(22) Filed: May 9, 2012

(65) Prior Publication Data

US 2012/0288873 A1    Nov. 15, 2012

Related U.S. Application Data

(60) Provisional application No. 61/483,941, filed on May 9, 2011.

(51) Int. Cl.
| | |
|---|---|
| *G01N 33/573* | (2006.01) |
| *A61K 35/50* | (2006.01) |
| *A61K 35/14* | (2006.01) |
| *A61K 35/413* | (2006.01) |
| *A61K 38/00* | (2006.01) |
| *A61P 25/00* | (2006.01) |

(52) U.S. Cl.
USPC ............ 435/7.4; 424/529; 424/528; 514/71.7

(58) Field of Classification Search
None
See application file for complete search history.

(56) References Cited

U.S. PATENT DOCUMENTS

2009/0305259 A1   12/2009  Madri et al.

OTHER PUBLICATIONS

Holmes and Cox (2011) "Comparative structures and evolution of vertebrate carboxyl ester lipase (CEL) genes and proteins with a major role in reverse cholesterol transport" Cholesterol 2011:1-15.*
Kolla et al. (2010) "quantitative proteomics analysis of maternal plasma in down syndrome using isobaric tagging reagent (itraq)" J Biomedicine Biotechnology 2010:1-10.*
Shimamura et al. (2005) "Overexpressoin of MUC13 is associated with intestinal-type gastric cancer" Cancer Sci 96(5):265-273.*
Webpage from Uniprot accessed on Jan. 9, 2013 at uniprot.org/uniprot/P05067.*
Canfield M. A., et al. National estimates and race/ethnic-specific variation of selected birth defects in the united states, 1999-2001. Birth Defects Res A Clin Mol Teratol 2006;76:747-56.
Antonarakis S. E., et al. Chromosome 21 and down syndrome: From genomics to pathophysiology. Nat Rev Genet 2004;5:725-38.

(Continued)

*Primary Examiner* — Jeffrey Stucker
*Assistant Examiner* — Adam M Weidner
(74) *Attorney, Agent, or Firm* — Bereskin & Parr LLP; Noel Courage; Carmela DeLuca

(57) ABSTRACT

The disclosure includes assays and methods for screening for risk of Down syndrome and/or trisomy 21 in a fetus. The assays and methods comprise determining the level of at least one biomarker selected from mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides in a test biological sample from a pregnant subject, wherein a decreased level of MUC13, CEL, DPP4, and/or CPA1 polypeptide and/or an increased level of APP and/or TNC-C polypeptide in the test biological sample compared to a corresponding reference biomarker polypeptide level indicates an increased risk of Down syndrome or trisomy 21 in the fetus. The disclosure also includes assays, compositions, immunoassays, and kits for performing the methods disclosed herein.

17 Claims, 16 Drawing Sheets

(56) References Cited

OTHER PUBLICATIONS

Malone F. D., et al. First-trimester or second-trimester screening, or both, for down's syndrome. N Engl J Med 2005;353:2001-11.
Haddow J. E., et al. Prenatal screening for down's syndrome with use of maternal serum markers. N Engl J Med 1992;327:588-93.
Halliday J. L., et al. New estimates of down syndrome risks at chorionic villus sampling, amniocentesis, and livebirth in women of advanced maternal age from a uniquely defined population. Prenat Diagn 1995;15:455-65.
Cho C. K., et al. Proteomics analysis of human amniotic fluid. Mol Cell Proteomics 2007;6:1406-15.
Park S. J., et al. Proteome analysis of human amnion and amniotic fluid by two-dimensional electrophoresis and matrix-assisted laser desorption/ionization time-of-flight mass spectrometry. Proteomics 2006;6:349-63.
Gravett M. G., et al. Diagnosis of intra-amniotic infection by proteomic profiling and identification of novel biomarkers. Jama 2004;292:462-9.
Cho, Chan-Kyung J., et al. Amniotic Fluid Proteome Analysis from Down Syndrome Pregnancies for Biomarker Discovery. Journal of Proteome Research 2010, 9, 3574-3582.
Perluigi M., et al. Oxidative stress occurs early in down syndrome pregnancy: A redox proteomics analysis of amniotic fluid. Proteomics Clin Appl 2011;5:167-78.
Cheng P. J., et al. Differential proteomics analysis of amniotic fluid in pregnancies of increased nuchal translucency with normal karyotype. Prenat Diagn 2011;31:274-81.
Whiteaker J. R., et al. Evaluation of large scale quantitative proteomic assay development using peptide affinity-based mass spectrometry. Mol Cell Proteomics 2011: e-pub ahead of print.
Drabovich A. P., et al. Combinatorial peptide libraries facilitate development of multiple reaction monitoring assays for low-abundance proteins. J Proteome Res 2010;9:1236-45.
Cho C. K., et al. Application of proteomics to prenatal screening and diagnosis for aneuploidies. Clin Chem Lab Med 2011;49:33-41.
Anderson N. L., et al. Mass spectrometric quantitation of peptides and proteins using stable isotope standards and capture by antipeptide antibodies (siscapa). J Proteome Res 2004;3:235-44.
Soini Y., et al. Expression of mmp2, mmp9, mt1-mmp, timp1, and timp2 mrna in valvular lesions of the heart. J Pathol 2001;194:225-31.
Brown D. L., et al. Identification of 92-kd gelatinase in human coronary atherosclerotic lesions. Association of active enzyme synthesis with unstable angina. Circulation 1995;91:2125-31.
Yang Z., et al. Extracellular matrix metalloproteinase 2 levels are regulated by the low density lipoprotein-related scavenger receptor and thrombospondin 2. J Biol Chem 2001;276:8403-8.16. Roher AE, Kasunic TC, Woods AS, Cotter RJ, Ball MJ, Fridman R. Proteolysis of a beta peptide from alzheimer disease brain by gelatinase a. Biochem Biophys Res Commun 1994;205:1755-61.
Yankner B. A., et al. Amyloid beta-protein toxicity and the pathogenesis of alzheimer disease. J Biol Chem 2009;284:4755-9.
Horstmann S., et al. Matrix metalloproteinases in peripheral blood and cerebrospinal fluid in patients with alzheimer's disease. Int Psychogeriatr;22:966-72.
Bellini C., et al. Nuchal translucency and lymphatic system maldevelopment. J Perinat Med 2009;37:673-6.
Shin J. W., et al. Lymphatic-specific expression of dipeptidyl peptidase iv and its dual role in lymphatic endothelial function. Exp Cell Res 2008;314:3048-56.
Ikushima H., et al. Internalization of cd26 by mannose 6-phosphate/insulin-like growth factor ii receptor contributes to t cell activation. Proc Natl Acad Sci U S A 2000;97:8439-44.
Kodvawala A., et al. Carboxyl ester lipase expression in macrophages increases cholesteryl ester accumulation and promotes atherosclerosis. J Biol Chem 2005;280:38592-8.
Bocconi L., et al. Trisomy 21 is associated with hypercholesterolemia during intrauterine life. Am J Obstet Gynecol 1997;176:540-3.
Prasher V. P., et al. Total serum cholesterol levels and alzheimer's dementia in patients with down syndrome. Int J Geriatr Psychiatry 2008;23:937-42.
Williams S. J., et al. Muc13, a novel human cell surface mucin expressed by epithelial and hemopoietic cells. J Biol Chem 2001;276:18327-36.
Chauhan S. C., et al. Expression and functions of transmembrane mucin muc13 in ovarian cancer. Cancer Res 2009; 69:765-74.
Walsh M. D., et al. The muc13 cell surface mucin is highly expressed by human colorectal carcinomas. Hum Pathol 2007;38:883-92.
Moehle C., et al. Aberrant intestinal expression and allelic variants of mucin genes associated with inflammatory bowel disease. J Mol Med 2006;84:1055-66.
Werner M., et al. Clinical utility and validation of emerging biochemical markers for mammary adenocarcinoma. Clin Chem 1993;39:2386-2396.
Togami S., et al. Expression of mucin antigens (MUC1 and MUC16) as a prognostic factor for mucinous adenocarcinoma of the uterine cervix. Journal of Obstet Gynecol Res 2010;36:588-597.
Pinheiro S. P., et al. (2010) Anti-MUC1 antibodies and ovarian cancer risk: prospective data from the Nurses' Health Studies. Cancer Epidemiol Biomark Prev 2010;19:1595-601.
Cohen, E. D., et al. Wnt signaling regulates smooth muscle precursor development in the mouse lung via a tenascin C/PDGFR pathway. J. Clin. Invest. 2009, 119 (9), 2538-49.
Imanaka-Yoshida, K., et al. The dynamic expression of tenascin-C and tenascin-X during early heart development in the mouse. Differentiation 2003, 71 (4-5), 291-8.
Ishii, K., et al. Role of stromal tenascin-C in mouse prostatic development and epithelial cell differentiation. Dev. Biol. 2008, 324 (2), 310-9.
Papadopoulos, N., et al. Induction of hepatic hematopoiesis with tenascin-C expression during the second trimester of development. Eur. J. Obstet. Gynecol. Reprod. Biol. 2004, 113 (1), 56-60.
Camacho, C., et al. Blast+: architecture and applications. BMC Bioinformatics 2009, 10, 421.
MacLean, B., et al. Skyline: an open source document editor for creating and analyzing targeted proteomics experiments. Bioinformatics 2010, 26, 966-8.
Spencer, K., et al. Biochemical markers of trisomy 21 in amniotic fluid. Prenat. Diagn. 1997, 17, 31-7.
Maher, D. M., et al. Mucin 13: structure, function, and potential roles in cancer pathogenesis. Mol. Cancer Res. 2011, 9, 531-7.
Hui, D. Y., al. et al. Lipoamidase activity in normal and mutagenized pancreatic cholesterol esterase (bile salt-stimulated lipase). Biochem. J. 1993, 291, 65-9.
Martinez-Morillo, Eduardo et al. Development of selected reaction monitoring assays for quantification of biochemical markers of Down syndrome in amniotic fluid samples. Poster presented at the 4th Annual Symposum Canadian National Proteomics Network. Apr. 23, 2012.
Martinez-Morillo, Eduardo et al. Development of Selected Reaction Monitoring Assays for Quantification of Biochemical Markers of Down Syndrome in Amniotic Fluid Sampleas. Abstract presented at the 4th Annual Symposum Canadian National Proteomics Network. Apr. 23, 2012.

\* cited by examiner

SEQUENCE LISTING

```
<160> NUMBER OF SEQ ID NOS: 17

<210> SEQ ID NO 1
<211> LENGTH: 12
<212> TYPE: PRT
<213> ORGANISM: Homo Sapien

<400> SEQUENCE: 1

Leu Gly Leu Leu Gly Asp Ser Val Asp Ile Phe Lys
1               5                   10

<210> SEQ ID NO 2
<211> LENGTH: 14
<212> TYPE: PRT
<213> ORGANISM: Homo Sapien

<400> SEQUENCE: 2

Ser Ser Ser Ser Asn Phe Leu Asn Tyr Asp Leu Thr Leu Arg
1               5                   10

<210> SEQ ID NO 3
<211> LENGTH: 11
<212> TYPE: PRT
<213> ORGANISM: Homo Sapien

<400> SEQUENCE: 3

Trp Glu Tyr Tyr Asp Ser Val Tyr Thr Glu Arg
1               5                   10

<210> SEQ ID NO 4
<211> LENGTH: 11
<212> TYPE: PRT
<213> ORGANISM: Homo Sapien

<400> SEQUENCE: 4

Ile Ser Val Ala Asp Glu Ala Gln Val Gln Lys
1               5                   10

<210> SEQ ID NO 5
<211> LENGTH: 19
<212> TYPE: PRT
```

```
<213> ORGANISM: Homo Sapien

<400> SEQUENCE: 5

Ile Ile Gly Tyr Thr Pro Asp Leu Asp Pro Glu Thr Val Asp Ala
1               5                   10                  15

Phe Ala Arg

<210> SEQ ID NO 6
<211> LENGTH: 16
<212> TYPE: PRT
<213> ORGANISM: Homo Sapien

<400> SEQUENCE: 6

Ala Leu Ser Met Cys Pro Pro Ser Pro Leu Gly Cys Glu Leu Val Lys
1               5                   10                  15

<210> SEQ ID NO 7
<211> LENGTH: 21
<212> TYPE: PRT
<213> ORGANISM: Homo Sapien

<400> SEQUENCE: 7

Gly Ala Phe Tyr Leu Leu Gly Glu Ala Tyr Phe Ile Gln Pro Leu Pro
1               5                   10                  15

Ala Ala Ser Glu Arg
            20

<210> SEQ ID NO 8
<211> LENGTH: 16
<212> TYPE: PRT
<213> ORGANISM: Homo Sapien

<400> SEQUENCE: 8

Glu Val Asn Val Ser Pro Cys Pro Thr Gln Pro Cys Gln Leu Ser Lys
1               5                   10                  15

<210> SEQ ID NO 9
<211> LENGTH: 14
<212> TYPE: PRT
<213> ORGANISM: Homo Sapien

<400> SEQUENCE: 9

Glu His Ala Val Glu Gly Asp Cys Asp Phe Gln Leu Leu Lys
1               5                   10

<210> SEQ ID NO 10
<211> LENGTH: 13
<212> TYPE: PRT
<213> ORGANISM: Homo Sapien

<400> SEQUENCE: 10

Tyr Val Ile Ser Gln Gly Asn Asp Asp Ser Val Phe Arg
1               5                   10

<210> SEQ ID NO 11
<211> LENGTH: 13
<212> TYPE: PRT
<213> ORGANISM: Homo Sapien

<400> SEQUENCE: 11

Glu Leu Gln Glu Thr Asn Ala Ala Leu Gln Asp Val Arg
1               5                   10

<210> SEQ ID NO 12
```

```
<211> LENGTH: 13
<212> TYPE: PRT
<213> ORGANISM: Homo Sapien

<400> SEQUENCE: 12

Asp Gly Ala Pro Cys Ile Phe Gly Gly Thr Val Tyr Arg
1               5                   10

<210> SEQ ID NO 13
<211> LENGTH: 9
<212> TYPE: PRT
<213> ORGANISM: Homo Sapien

<400> SEQUENCE: 13

Val Leu Asp Ala Leu Gln Ala Ile Lys
1               5

<210> SEQ ID NO 14
<211> LENGTH: 10
<212> TYPE: PRT
<213> ORGANISM: Homo Sapien

<400> SEQUENCE: 14

Asp Gly Ala Gly Asp Val Ala Phe Val Lys
1               5                   10

<210> SEQ ID NO 15
<211> LENGTH: 12
<212> TYPE: PRT
<213> ORGANISM: Homo Sapien

<400> SEQUENCE: 15

Leu Ser Glu Pro Ala Glu Leu Thr Asp Ala Val Lys
1               5                   10

<210> SEQ ID NO 16
<211> LENGTH: 17
<212> TYPE: PRT
<213> ORGANISM: Homo Sapien

<400> SEQUENCE: 16

Val Leu Gln Gly Val Leu Pro Ala Leu Pro Gln Val Val Cys Asn Tyr
1               5                   10                  15

Arg

<210> SEQ ID NO 17
<211> LENGTH: 15
<212> TYPE: PRT
<213> ORGANISM: Homo Sapien

<400> SEQUENCE: 17

Tyr Gly Phe Leu Leu Pro Ala Ser Gln Ile Ile Pro Thr Ala Lys
1               5                   10                  15
```

BIOMARKERS FOR THE DETECTION AND SCREENING OF DOWN SYNDROME

CROSS REFERENCE TO RELATED APPLICATIONS

This non-provisional application claims priority from U.S. provisional application U.S. 61/483,941 filed on May 9, 2011, which is incorporated herein by reference in its entirety.

SEQUENCE LISTING

A computer readable form of the Sequence Listing "10723-416SL.txt" (3,511 bytes), submitted via EFS-WEB and created on May 9, 2012, is herein incorporated by reference.

FIELD

The field of the disclosure relates to prenatal screening for Down syndrome (DS) using polypeptide biomarker levels. The disclosure specifically relates to assays, methods, compositions and kits for detecting the biomarkers in maternal blood and/or amniotic fluid.

BACKGROUND OF THE DISCLOSURE

Down syndrome, or trisomy 21, occurs when an individual inherits three copies of chromosome 21. Trisomy 21 is the most common chromosomal abnormality, occurring with an incidence of approximately 1 in 750 live births (1). The molecular pathogenesis of this condition is unclear and no direct genotype-phenotype associations have been established. This abnormality leads to the development of complex clinical features and symptoms, including: mental retardation, Alzheimer's disease, seizures, thyroid disorders, cardiac defects, an increased risk of leukemia, infertility, gastrointestinal defects and early aging (2). The risk of trisomy 21 increases with advanced maternal age, when an abnormal parental karyotype is present and with history of having another child or previous pregnancy with Down syndrome (3).

Current screening methods for trisomy 21 incorporate a physical marker with markers found in maternal serum. The physical marker, fetal nuchal translucency (NT), is measured by ultrasound. Serum markers, pregnancy-associated plasma protein A (PAPP-A) and human chorionic gonadotropin beta (β-hCG) are measured in maternal serum during the first trimester. Alpha fetoprotein (AFP), unconjugated estriol (uE3), β-hCG and inhibin A are measured in maternal serum during the second trimester. These combined markers have a detection rate of 90-95% with a 5% false positive rate (4). The screening markers which are currently available are not ideal. They require first and second trimester procedures and they offer relatively low specificity, producing many false positive results which require invasive follow-up by amniocentesis (4).

SUMMARY

Down syndrome, or trisomy 21, is the most common chromosomal abnormality, leading to development of complex clinical features and symptoms. Current screening methods for trisomy 21 during pregnancy lack specificity, resulting in a large number of false positives, requiring invasive follow-up by amniocentesis.

Mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides are demonstrated herein to be differentially present in amniotic fluid (AF) and/or maternal blood from pregnant subjects carrying trisomy 21-affected compared to unaffected fetuses.

Accordingly, an aspect of the disclosure includes a method of screening for an increased risk of Down syndrome and/or trisomy 21 in a fetus, the method comprising determining a level of at least one biomarker selected from MUC13, CEL, DPP4, CPA1, APP and TNC-C polypeptides in a test biological sample from a pregnant subject; wherein a decreased level of MUC13, CEL, DPP4, and/or CPA1 polypeptide and/or an increased level of APP and/or TNC-C polypeptide in the test biological sample compared to a corresponding reference biomarker polypeptide level indicates an increased risk of Down syndrome and/or trisomy 21 in the fetus.

In an embodiment, the method comprises the steps of:
a) determining a level of at least one biomarker selected from MUC13, CEL, DPP4, CPA1, APP and TNC-C polypeptide in a test biological sample from a pregnant subject; and
b) comparing the level with a corresponding reference biomarker polypeptide level; and
c) identifying if the level is increased or decreased compared to the corresponding reference biomarker polypeptide level;

wherein a decreased level of MUC13, CEL, DPP4, and/or CPA1 polypeptide and/or an increased level of APP and/or TNC-C polypeptide in the test biological sample compared to the reference biomarker polypeptide level indicates an increased risk of Down syndrome or trisomy 21 in the fetus.

In another embodiment, the method comprises the steps of:
a) obtaining a test biological sample from a pregnant subject,
b) measuring or quantifying the level of at least one biomarker selected from mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides in a test biological sample from a pregnant subject,
c) comparing the measured or quantified amount of the at least one biomarker with a corresponding reference biomarker polypeptide level, and, if the level of MUC13, CEL, DPP4, and/or CPA1 polypeptide is decreased and/or the amount of APP and/or TNC-C polypeptide is increased in the test biological sample compared to the reference biomarker polypeptide level, identifying the subject as having an increased probability of Down syndrome and/or trisomy 21 in the fetus.

In an embodiment, the at least one biomarker comprises MUC13, CEL, and/or CPA1.

In an embodiment, the at least one biomarker comprises MUC13.

In an embodiment, the at least one biomarker comprises MUC13 and CPA1.

In an embodiment, the at least one biomarker comprises MUC13 and CEL.

In still another embodiment, the biological sample is selected from blood or a fraction thereof, urine and amniotic fluid.

In an embodiment, the blood or fraction thereof is maternal blood or fraction thereof.

In an embodiment, the blood fraction is plasma or serum.

In an embodiment, the method described herein further comprises determining the level of at least one biomarker selected from pregnancy-associated plasma protein A (PAPP-A), human chorionic gonadotropin beta (β-hCG), Alpha fetoprotein (AFP), unconjugated estriol (uE3) and inhibin A polypeptides in the test biological sample.

In an embodiment, the at least one biomarker comprises MUC 13 and AFP, MUC 13 and β-hCG, and/or CPA1 and AFP.

In an embodiment, determining the level of the at least one biomarker comprises using an immunoassay and/or mass spectrometric methods.

Another aspect of the disclosure includes an assay comprising:
  a) measuring or quantifying the level of at least one biomarker selected from mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides in a test biological sample from a pregnant subject; and
  b) comparing the measured or quantified level of the at least one biomarker with a corresponding reference biomarker polypeptide level, and if the level of MUC13, CEL, DPP4, and/or CPA1 polypeptide is decreased and/or the level of APP and/or TNC-C polypeptide is increased in the test biological sample compared to the reference biomarker polypeptide level, identifying the subject as having an increased probability of Down syndrome and/or trisomy 21 in the fetus.

A further aspect of the disclosure includes a kit for screening for risk of Down syndrome and/or trisomy 21 in a fetus comprising:
  a) an antibody that specifically binds a biomarker selected from MUC13, CEL, DPP4, CPA1, APP and TNC-C polypeptides; and
  b) one or more of instructions for performing an assay or method described herein; one or more kit controls; sterile collection tubes; microtiter wells and wash solution.

In an embodiment, the kit comprises reagents for an immunoassay.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION

I. Definitions

Figure 1:
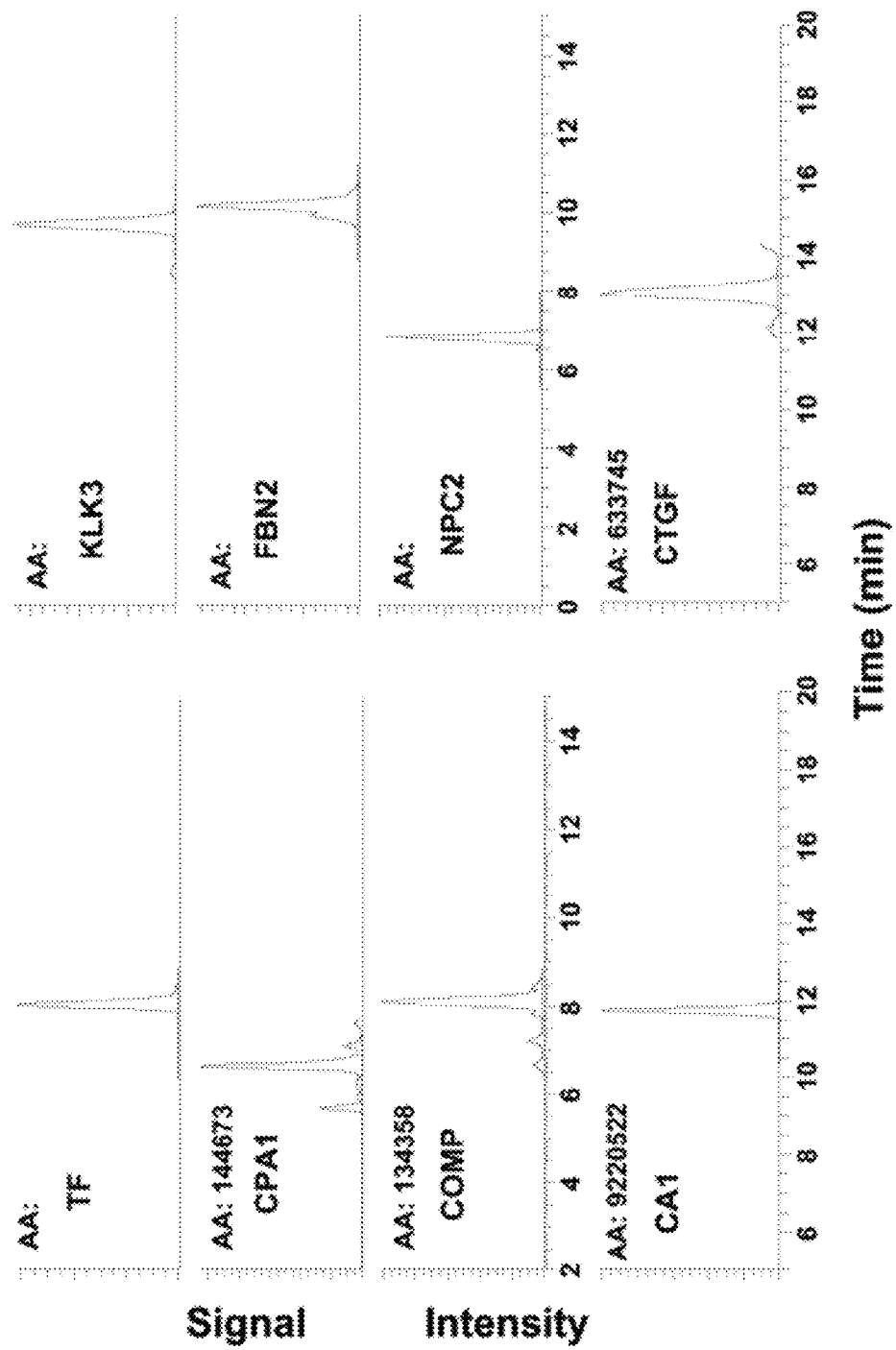
FIG. 1. Quantification of thirteen candidates and serotransferrin in individual AF samples for comparison between DS versus control groups. Normalized area of the peaks were calculated by dividing peak intensity of each peptide by that of internal standard (heavy peptide LSEPAELTDAVK of KLK3 (SEQ ID NO:15)) in each sample. Low variation of TF in individual samples could serve as an indirect indicative that sample preparation protocol was consistent for all individual samples assayed.
Figure 1:
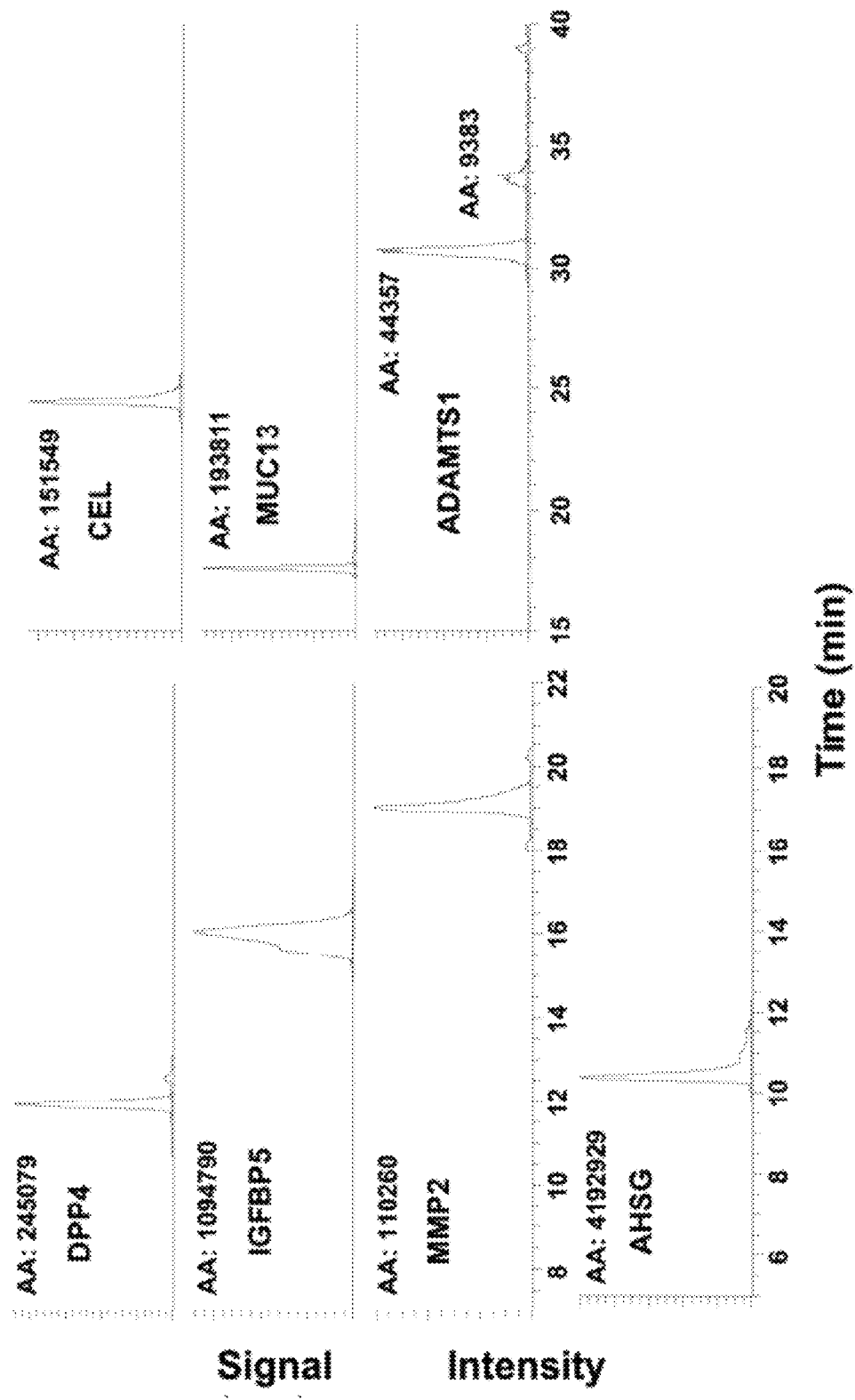

The phrase "screening for risk of Down syndrome" or "screening for risk of trisomy 21" refers to a screening assay, method or process that aids in the determination of whether a fetus has an increased probability of having Down syndrome or trisomy 21, involving detecting the level of one or more biomarkers described herein. For example, detection of decreased polypeptide levels of at least one biomarker selected from MUC13, DPP4, CPA1, and/or CEL and/or an increased level of APP and/or TNC-C in a test biological sample compared to a corresponding reference biomarker polypeptide level is indicative of an increased risk of Down syndrome and/or trisomy 21 in the fetus.

The term "subject" as used herein refers to any member of the animal kingdom, preferably a human being including for example a human fetus or a human fetus with Down syndrome or trisomy 21.

The term "level" as used herein refers to an amount (e.g. relative amount or concentration) of biomarker that is detectable, measurable or quantifiable in a test biological sample and/or a reference biological sample. For example, the level can be a concentration such as µg/L or ng/L, or a relative amount such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 10, 15, 20, 25, and/or 30 times more or less than a reference biomarker polypeptide level. The reference biomarker polypeptide level, can for example, be the average or median level in a plurality of chromosome 21 normal reference biological samples (e.g. maternal serum or amniotic fluid samples from subjects carrying a fetus with normal chromosome 21 karyotype). The level of biomarker can include, for example, the level of soluble biomarker (e.g. non-cell associated biomarker such as cleaved, secreted, released, or shed biomarker) detectable in a biological fluid such as blood or a fraction thereof (e.g. the level of serum biomarker).

The term "reference biological sample" or "negative control" as used herein refers to a sample from an individual or a group of individuals who are known as not carrying a trisomy 21- or Down syndrome-affected fetus, such as a blood sample or amniotic fluid sample. Similarly, the term "reference biomarker polypeptide level" as used herein refers to a biomarker level or value, such as a cut-off value, corresponding to such a sample or group of samples, wherein a polypeptide level of biomarker selected from MUC13, DDP4, CPA1, and/or CEL in a test biological sample at or above such value and/or with a polypeptide level of biomarker selected from APP and/or TNC-C in AF in a test biological sample at or below such a value indicates a decreased risk of Down syndrome, and a polypeptide level of biomarker selected from MUC13, DDP4, CPA1, and/or CEL in a test biological sample below such value and/or with a polypeptide level of biomarker selected from APP and/or TNC-C in a test biological sample above such value indicates an increased risk of Down syndrome. In another example, the reference biomarker polypeptide level can be a value that corresponds to the median level of the biomarker in a set of samples from pregnant subjects carrying chromosome 21 normal fetuses. In addition, the reference biomarker polypeptide level can be for example determined in a reference biological sample of the same type as the sample of the pregnant subject being tested. For example, both the reference biological sample and the sample (e.g. test biological sample) can comprise serum samples.

The term "positive control sample" as used herein refers to a sample from an individual or a group of individuals who are known as carrying a trisomy 21- or Down syndrome-affected fetus, such as a blood sample or amniotic fluid sample. Similarly, the term "positive control polypeptide level" as used herein refers to a biomarker level or value, corresponding to such a sample or group of samples. In another example, the reference biomarker polypeptide level can be a value that corresponds to the median level of the biomarker in a set of samples from pregnant subjects carrying trisomy 21 fetuses. In addition, the positive control polypeptide level can be for example determined in a reference biological sample of the same type as the sample of the pregnant subject being tested. For example, both the positive control sample and the test sample (e.g. test biological sample) can comprise serum samples The term "baseline level" as used herein refers to a level in a biological sample that is used for comparison to a biological sample taken at a later time point from the same subject, for example a pregnant subject. For example, in assays and methods related to monitoring biomarker expression, for example throughout gestation, "base-line level" can refer to a level of a biomarker in a test biological sample and/or reference biological sample obtained prior to a subsequent test biological sample and/or reference biological sample, e.g. a base-line sample can be taken in the first trimester and compared to a second trimester sample.

The term "biomarker" as used herein refers to a polypeptide (including for example glycosylated polypeptides, and/or polypeptide fragments) whose levels are associated with risk of Down syndrome, including MUC13, DPP4, CPA1, CEL, APP and/or TNC-C also referred to as "biomarkers of the disclosure". The biomarkers are differentially present (e.g. expressed secreted, cleaved and/or otherwise present) in pregnant subjects carrying a fetus with Down syndrome, the level of one or more of which can be used to distinguish fetuses with an increased risk of Down syndrome and fetuses that do not have an increased risk of Down syndrome.

The term biomarker includes without limitation, soluble biomarkers and/or serum biomarkers.

The term "fragment" as used herein in relation to a biomarker means a portion of a full-length biomarker protein, and depending on the length of the protein comprises for example at least 8, 10, 20, 30, 40, 50, 60, 70, 80, 90, or 100 amino acids. The fragment can for example, be an extracellular portion of the polypeptide. The fragment can include the full length protein less at least 8, 10, 20, 30, 40, 50, 60, 70, 80, 90, or 100 amino acids.

The term "corresponding reference biomarker polypeptide level" as used herein refers to the same biomarker or biomarkers as the biomarker for which the level(s) are being determined. For example, in assays and methods that determine a level of MUC13 in the test biological sample, the corresponding reference biomarker polypeptide level is the level of MUC13 in a reference sample or samples, optionally previously determined to provide a cut-off level. As another example where, MUC13 and DPP4 levels are being determined, the corresponding reference biomarker polypeptide level is MUC13 and DPP4 respectively.

The term "biomarker specific detection agent" or "detection agent" refers to an agent that selectively binds its cognate biomarker compared to another molecule and which can be used to detect a level and/or the presence of the biomarker. A biomarker specific detection agent can include binding polypeptides such as antibodies which can for example be used with immunohistochemistry (IHC), ELISA, immunofluorescence, radioimmunoassay, dot blotting, FACS and protein microarray to detect the expression level of a biomarker associated with Down syndrome or trisomy 21. Similarly, "an antibody or fragment thereof" (e.g. binding fragment), that specifically binds a biomarker refers to an antibody or fragment that selectively binds its cognate biomarker compared to another molecule. "Selective" is used contextually, to characterize the binding properties of an antibody. An antibody that binds specifically or selectively to a given biomarker or epitope thereof will bind to that biomarker and/or epitope either with greater avidity or with more specificity, relative to other, different molecules. For example, the antibody can bind 3-5 fold, 5-7 fold, 7-10, 10-15, 5-15, or 5-30 fold more efficiently to its cognate biomarker compared to another molecule. The "detection agent" can for example be coupled to or labeled with a detectable marker. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The term "soluble biomarker" as used herein refers to a biomarker that is detectable in a biological fluid, such as blood or blood fraction such as serum and/or plasma, urine and/or amniotic fluid. For example, without wishing to be bound to theory, a soluble biomarker can be expressed, cleaved, secreted, or shed from a cell and/or these processes can be interrupted such that levels become elevated or decreased, for example in biological fluid such as serum or amniotic fluid, through several possible mechanisms. Molecules can be released into the circulation or amniotic fluid through aberrant shedding and/or secretion from cells. Proteins and other molecules can also be cleaved from the extracellular surface of tumour cells by proteases.

The term "serum biomarker" as used herein refers to a soluble biomarker detectable in blood or a blood fraction such as plasma and/or serum.

The term "determining an expression level" or "determining a level" or "measuring or quantifying a level" as used in reference to a biomarker means: the application of a biomarker specific detection agent such as an antibody and/or the application of a method to a sample, for example a test biological sample and/or a reference biological sample, for ascertaining or measuring quantitatively, semi-quantitatively or qualitatively the amount of a biomarker. For example, a level of a biomarker can be determined by a number of methods using different assays including for example mass spectrometric based assays, including for example MS, MS/MS, LC-MS/MS, SRM etc where a peptide of a biomarker is labeled and the amount of labeled biomarker peptide is ascertained, immunoassays including for example immunohistochemistry, ELISA, e.g. sandwich type ELISA, Western blot, immunoprecipitation, immunofluorescence, radioimmunoassay, dot blotting, FACS and the like, where a biomarker specific detection agent such as an antibody for example, a labeled antibody, specifically binds the biomarker (e.g. an epitope therein) and permits for example relative or absolute ascertaining of the amount of polypeptide biomarker.

The term "MS" refers to mass spectrometry.

The term "MS/MS" refers to tandem mass spectrometry.

The term "1D LC-MS/MS" refers to 1-dimensional liquid chromatography tandem mass spectrometry using for example a LTQ-Orbitrap XL apparatus.

The term "2D LC-MS/MS" refers to 2-dimensional liquid chromatography tandem mass spectrometry using for example a LTQ-Orbitrap XL apparatus.

The term "SRM" refers to selective reaction monitoring which is a mass spectrometry approach to the quantitative detection of selected proteins. The assay can for example be multiplexed (e.g. MRM).

The term "biological sample" as used herein refers to any biological fluid, cell or tissue sample from a subject (e.g. test subject), which can be assayed for biomarkers (e.g. carbohydrate antigen, and/or polypeptide expression products), such as soluble biomarkers. For example the sample is or can comprise blood, or a fraction thereof such as serum or plasma, or amniotic fluid.

The term "biological fluid" as used herein refers to any body fluid, which can comprise cells or be substantially cell free, which can be assayed for biomarkers, including for example blood including serum and plasma fractions, urine and/or amniotic fluid.

The term "antibody" as used herein is intended to include monoclonal antibodies, polyclonal antibodies, and chimeric antibodies. The antibody may be from recombinant sources and/or produced in transgenic animals. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Antibody fragments mean binding fragments.

Antibodies having specificity for a specific protein, such as the protein product of a biomarker of the disclosure, may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

The term "kit control" as used herein means a suitable assay control useful when determining a level of a biomarker associated with Down syndrome or trisomy 21. For example, when the kit is for a MRM/SRM based assay, the kit control is optionally a quantity of a peptide fragment of a biomarker polypeptide that can for example be used to prepare a standard curve, for example serotransferrin (TF), for example the peptide of SEQ ID NO:14, and/or prostate-specific antigen (KLK3), for example the peptide of SEQ ID NO:15. The kit control can, as another example, be a quantity of recombinant biomarker such as recombinant MUC13 which can serve as a positive control. As an alternative example, where the kit is for detecting polypeptide levels by an immunohistochemical assay, the kit control can comprise an antibody control, useful for example for detecting non-specific binding and/or a quantity of protein (e.g. BSA) for standardizing the amount of protein in the sample. The kit control is optionally a serum sample corresponding for example to a non-pregnant subject, or corresponding to a subject pregnant with a trisomy-21 affected or unaffected fetus and/or a known quantity of biomarker (e.g. MUC13).

The term "reproducible difference" as used herein refers to a difference in for example protein levels of a biomarker in a test biological sample compared to a reference biomarker polypeptide level, wherein the difference can be replicated on more than one occasion using either multiple samples from the subject or multiple replicates from the same sample from the subject or both. For example, a difference will be reproducible if the polypeptide level of a biomarker selected from MUC13, DPP4, CPA1, CEL, and/or combinations thereof in a test biological sample are shown to be decreased compared to a corresponding reference biomarker polypeptide level or levels or the polypeptide level of a biomarker selected from APP, TNC-C, and/or combinations thereof in a test biological sample are shown to be increased compared to a corresponding reference biomarker polypeptide level in at least two runs of the assay performed on either multiple test biological samples taken from the same pregnant subject. Similarly, a difference will be reproducible if the polypeptide level of a biomarker selected from MUC 13, DPP4, CPA1, and/or CEL polypeptides in a test biological sample are shown to be decreased compared to a corresponding reference biomarker polypeptide level or the protein levels a biomarker selected from APP and/or TNC-C polypeptide in a test biological sample are shown to be increased compared to a corresponding reference biomarker polypeptide level in at least two runs of the assay performed on multiple replicates taken from a single test biological sample from the same pregnant subject.

The term "MUC13" as used herein refers to "mucin 13", a protein that is highly expressed in epithelial tissues, particularly along gastrointestinal tracts, and includes without limitation, all known MUC13 molecules, including human, naturally occurring variants and those deposited in Genbank, for example, with accession number Q9H3R2 and/or IP100011448, each of which is herein incorporated by reference. Several splice variants of MUC13 are known. MUC13 can be secreted and can be cleaved into alpha and beta subunits.

The term "DPP4" as used herein refers to "dipeptidyl peptidase 4", which can be a cell surface glycoprotein receptor mainly expressed in lymphatic vessels, or a soluble form (e.g. sDPP4) created by proteolytic cleavage of the membrane form and includes without limitation, all known DPP4 molecules, including human, naturally occurring variants and those deposited in Genbank, for example, with accession number P27487, IP100018953, IP1100924974, IP100927124 and/or IP100924746, each of which is herein incorporated by reference.

The term "CPA1" as used herein refers to "carboxypeptidase A1", and includes without limitation, all known CPA1 molecules, including human, naturally occurring variants and those deposited in Genbank, for example, with accession number P15085 and/or IP100009823, each of which is herein incorporated by reference. CPA1 zymogen is activated by proteolytic cleavage to produce an active form and CPA1 is an enzyme that cleaves amino acids from the C-terminus of proteins and peptides and for example preferentially cleaves aromatic peptide residues.

The term "CEL" as used herein refers to "bile salt-activated lipase", a secreted lipolytic protein that hydrolyzes cholesterol esters, triacylglycerols, and phospholipids, and includes without limitation, all known CEL molecules, including human, naturally occurring variants and including those deposited in Genbank, for example, with accession number P19835, IP100099670, IP100843810 and/or IP100218674, each of which is herein incorporated by reference. CEL is mainly produced in the mammary gland and pancreas. Its dysregulated expression in macrophages has been linked to promotion of atherosclerosis, indicating its importance in lipid regulation. CEL can comprise for example a signal sequence, and detection can be directed to CEL epitopes downstream of the signal peptide (e.g. epitopes in the secreted protein). For example, detection can be directed at the first ⅔ of the protein after the signal sequence.

The term "APP" as used herein refers to "amyloid precursor protein" and includes without limitation, all known APP molecules, including naturally occurring variants and including those deposited in Genbank, for example, with accession number IP100412681; IP1100412924; IP100394658, IP100909502; IP100914602; IP100219185; IP100219186; IP100006608; IP100219187; IP100219183 and/or IP100412568, each of which is herein incorporated by reference.

The term "TNC-C" as used herein refers to "tenascin-C" and includes without limitation, all known TNC-C molecules, including naturally occurring variants and including those deposited in Genbank, for example, with accession number IP100867560; IP100747950; IP100220213; IP100220212; IP100220214; IP100220216; IP100220211 and/or IP100031008, herein incorporated by reference.

The term "chromosome 21 normal fetus" as used herein refers to a fetus or that does not have Down syndrome or trisomy 21 and/or has a normal human chromosome 21 karyotype. A "chromosome 21 normal sample" is accordingly a sample associated with a chromosome 21 normal fetus e.g. a sample from a pregnant subject carrying a chromosome 21 normal fetus.

The term "trisomy 21" as used herein refers to a state where a subject's karyotype is characterized by a complete or partial triplication of human chromosome 21 (HSA21). Trisomy 21 is associated with "Down syndrome" also referred to as "Down's syndrome" or "DS". Trisomy 21 leads to complex clinical features and symptoms, for example mental retardation, Alzheimer's disease, seizures, thyroid disorders, cardiac defects, an increased risk of leukemia, infertility, gastrointestinal defects and early aging.

The term "first trimester" as used herein refers to the period of time within the first third of a pregnant subject's gestation. For example, the "first trimester" can be the period of time within the first three months, the first 12 weeks or about the first 90 days of gestation, for example human gestation.

The term "second trimester" as used herein refers to the period of time within the second third of a pregnant subject's gestation. For example, the "second trimester" comprises the period of time within the fourth through sixth months, $13^{th}$ through $27^{th}$ weeks, or about days 91 to 120 of gestation, for example human gestation.

The term "at least one" as used herein means one, two, three, four, five or more of elements, components, groups, integers, and/or steps for example one, two, three, four, five or six of MUC13, CEL, DPP4, CPA1, APP and TNC-C biomarkers and includes at least 2, at least 3, at least 4 and at least 5.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Assays and Methods

Disclosed herein are biomarkers for screening for risk of Down syndrome or trisomy 21 in a fetus. The screening markers which are currently available for Down syndrome or trisomy 21 may for example require first and second trimester procedures and/or offer relatively low specificity, producing many false positive results which require invasive follow-up by amniocentesis.

Amniotic fluid (AF) is rich in proteins which may reflect the well-being of the fetus. It was hypothesized that biomarkers for trisomy 21 exist in AF. A detailed comparison of AF from trisomy 21-affected pregnancies to AF from unaffected pregnancies was completed, with proteomic techniques using mass spectrometry and SRM. Several candidate trisomy 21 biomarkers were identified in AF, including mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C). MUC13, CEL, DPP4, and CPA1 were found to be present in lower levels in trisomy 21 AF samples compared to chromosome 21 normal fetuses. APP and TNC-C were found to be expressed at higher levels in trisomy 21 AF samples compared to chromosome 21 normal fetuses.

Accordingly, disclosed herein are assays and methods for screening for an increased risk of Down syndrome and/or trisomy 21 in a fetus using biomarkers, which are differentially present in a biological sample from a pregnant subject carrying a fetus having or not having Down syndrome or trisomy 21.

An aspect of the disclosure relates to an assay comprising the following steps:
a) measuring or quantifying the level of at least one biomarker selected from mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides in a test biological sample from a pregnant subject; and
b) comparing the measured or quantified level of the at least one biomarker with a corresponding reference biomarker polypeptide level, and if the level of MUC13, CEL, DPP4, and/or CPA1 polypeptide is decreased and/or the level of APP and/or TNC-C polypeptide is increased in the test biological sample compared to the reference biomarker polypeptide level, identifying the subject as having an increased probability of Down syndrome and/or trisomy 21 in the fetus.

In an embodiment, the assay is for use in a method described herein.

Another aspect of the disclosure includes a method of screening for an increased risk of Down syndrome or trisomy 21 in a fetus, the method comprising determining a level of at least one biomarker selected from MUC13, CEL, DPP4, CPA1, APP and TNC-C polypeptides in a test biological sample from a pregnant subject; wherein a decreased level of MUC13, CEL, DPP4, and/or CPA1 polypeptide and/or an increased level of APP and/or TNC-C polypeptide in the test biological sample compared to a corresponding reference biomarker polypeptide level indicates an increased risk of Down syndrome and/or trisomy 21 in the fetus.

In another embodiment, the disclosure includes a method for identifying a pregnant subject whose fetus is at risk of having Down syndrome and/or trisomy 21, the method comprising determining a level of at least one biomarker selected from MUC13, CEL, DPP4, CPA1, APP and TNC-C polypeptides in a test biological sample from a pregnant subject; wherein a decreased level of MUC13, CEL, DPP4, and/or CPA1 polypeptide and/or an increased level of APP and/or TNC-C polypeptide in the test biological sample compared to a corresponding reference biomarker polypeptide level indicates an increased risk of Down syndrome and/or trisomy 21 in the fetus.

In an embodiment, the method comprises the steps of:
a) determining a level of at least one biomarker selected from MUC13, CEL, DPP4, CPA1, APP and TNC-C polypeptide in a test biological sample from a pregnant subject;
b) comparing said level with a corresponding reference biomarker polypeptide level; and
c) identifying if the level is increased or decreased compared to the corresponding reference biomarker polypeptide level;
wherein a decreased level of MUC13, CEL, DPP4, and/or CPA1 polypeptide and/or an increased level of APP and/or TNC-C polypeptide in the test biological sample compared to the reference biomarker polypeptide level indicates an increased risk of Down syndrome and/or trisomy 21 in the fetus.

In another embodiment, the method comprises the steps of:
a) obtaining a test biological sample from a pregnant subject,
b) measuring or quantifying the level of at least one biomarker selected from mucin 13 (MUC13), bile salt-activated lipase (CEL), dipeptidyl peptidase 4 (DPP4), carboxypeptidase A1 (CPA1), amyloid precursor protein (APP) and tenascin-C (TNC-C) polypeptides in a test biological sample from a pregnant subject, c) comparing the measured or quantified amount of the at least one biomarker with a corresponding reference biomarker polypeptide level, and, if the level of MUC13, CEL, DPP4, and/or CPA1 polypeptide is decreased and/or the amount of APP and/or TNC-C polypeptide is increased in the test biological sample compared to the reference biomarker polypeptide level, identifying the subject as having an increased probability of Down syndrome and/or trisomy 21 in the fetus.

If for example, the level of MUC13, CEL, DPP4, and/or CPA1 polypeptide is not decreased and/or the amount of APP and/or TNC-C polypeptide is not increased in the test biological sample compared to the reference biomarker polypeptide level, the assay or method identifies the subject as not having an increased probability of Down syndrome and/or trisomy 21 in the fetus.

In an embodiment, the assay or method comprises determining for each selected biomarker, the level. In another embodiment, the method comprises measuring or quantifying the level for each selected biomarker. In an embodiment, 1, 2, 3, 4, 5 or biomarkers are selected from MUC13, CEL, DPP4, CPA1, APP and TNC-C.

In a further embodiment, the biomarkers are any two biomarkers or any three biomarkers selected from MUC13, CEL, DPP4, CPA1, APP and TNC-C. In another embodiment, the biomarkers are MUC13 and CPA1. In another embodiment, the biomarkers are MUC13 and CEL.

In an embodiment, the assay or method is further compared to a positive control.

In an embodiment, the assay or method is used to determine a probability of Down syndrome.

Accordingly, in another embodiment, the assay or method comprises determining a probability that a fetus has Down syndrome and/or trisomy 21 as opposed to not having Down syndrome and/or trisomy 21, the assay or method comprising, for each biomarker of a set of one or more biomarkers selected from MUC13, CEL, DPP4, CPA1, APP and TNC-C: (a) determining a level of the biomarker in a test biological sample from the pregnant subject, thereby generating test data; (b) providing positive control data representing biomarker levels in positive control samples, and providing control data representing biomarker levels in negative control subjects; and (c) determining a probability that the test data corresponds to the positive control data and not to the negative control data, wherein the probability that the test data corresponds to the positive control data and not to the negative control data represents the probability that the fetus has Down syndrome and/or trisomy 21 as opposed to not having Down syndrome and/or trisomy 21.

In an embodiment, the reference biomarker polypeptide level is a cut-off value determined from a group of reference biological samples. In an embodiment, the reference biomarker polypeptide level to which the test sample level is compared to, is a mean or average level, concentration or amount of biomarker polypeptide for a group of reference biological samples. The reference biological sample can for example, be confirmed as being from a pregnant subject or pregnant subjects with a chromosome 21 normal fetus by amniocentesis and fetal karyotype analysis, using techniques known in the art.

In an embodiment, the test biological sample is a sample from a pregnant subject in the first trimester. In another embodiment, the test biological sample is a sample from a pregnant subject in the second trimester. In an embodiment, the test biological sample is compared to a same trimester reference biological sample and/or reference polypeptide level corresponding to the same trimester as the test biological sample. In an embodiment, the test biological sample is from and the reference biological sample is from (and/or the reference biomarker polypeptide level corresponds to) a same gestational trimester, month or week. In an embodiment, the test biological sample is from a pregnant subject in a first trimester and the reference biological sample is from (and/or corresponding reference polypeptide level) one or more pregnant subjects in a first trimester. In another embodiment, the test biological sample is from a pregnant subject in a second trimester and the reference biological sample is from (and/or corresponding reference polypeptide level) one or more pregnant subjects in a second trimester. In another embodiment, the samples (or corresponding reference levels) are each from one or more pregnant subjects in a first, second, third, fourth, fifth, or sixth month of gestation. In an embodiment, the test biological sample is from a pregnant subject at about week 16 to 20 of gestation and the reference biological sample is from (and/or the reference biomarker polypeptide level corresponds to) one or more pregnant subjects at about week 16 to 20 of gestation. In still another embodiment, the samples are each from a pregnant subject in a first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$ or twenty-seventh week of gestation. In another embodiment, the test biological sample is a sample from a pregnant subject of about 30 to about 45 years of age. In yet another embodiment, the test biological sample is from a pregnant subject of about 30, 35, 36, 37, 38, 39, 40, 41, 42, 43, 44, or 45 years of age. In an embodiment, the reference sample if from and/or level corresponds to one or more subjects of about 30 to about 45 years of age or any age or range in between.

In another embodiment, the at least one biomarker is MUC13, CEL, DPP4, and/or CPA1. In an embodiment, the at least one biomarker is human MUC13, human CEL, human DPP4, and/or human CPA1. In another embodiment, the at least one biomarker comprises MUC13, optionally human MUC13.

As demonstrated in the Examples, MUC13 polypeptide levels were measured in serum from pregnant and non-pregnant women. MUC13 levels were also compared in maternal serum from women carrying trisomy 21-affected compared to unaffected fetuses. Serum samples were collected from non-pregnant (n=8) and pregnant women during the first (n=20) and second (n=25) trimesters of pregnancy. Samples were confirmed as being from unaffected (n=28) or from trisomy 21-affected (n=17) fetuses by amniocentesis and fetal karyotype analysis. Serum MUC13 protein levels were measured by ELISA. It is demonstrated for example, that MUC13 protein levels could be quantified in serum from pregnant women but were undetectable in most sera from non-pregnant women by ELISA. MUC13 levels appear to increase in maternal serum during pregnancy. MUC13 levels were significantly lower in serum from women in the first trimester of pregnancy who were carrying trisomy 21-affected compared to unaffected fetuses ($p<0.01$). MUC13 levels were also lower in serum from women in the second trimester of pregnancy but the differences did not reach statistical significance. In another embodiment, the at least one biomarker comprises CEL, optionally human CEL. In an embodiment, the at least one biomarker comprises DPP4, optionally human DPP4. In an embodiment, the at least one biomarker comprises CPA1, optionally human CPA1. In another embodiment, the at least one biomarker is selected from APP and TNC-C.

In another embodiment, the at least one biomarker comprises APP and TNC-C. In still another embodiment, the at least one biomarker comprises human APP and/or human TNC-C. In an embodiment, the at least one biomarker comprises APP, optionally human APP. In an embodiment, the at least one biomarker comprises TNC-C, optionally human TNC-C.

In an embodiment, the biological test sample is blood and/or a fraction thereof and the biomarker tested is selected from MUC13, CEL, DPP and/or CPA1. In an embodiment, the biological test sample is blood and/or a fraction thereof and the biomarker tested comprises and/or is MUC13.

In another embodiment, the biological test sample is amniotic fluid and the biomarker tested is selected from MUC13, CEL, DPP and/or CPA1 and/or APP and TNC-C.

In an embodiment, the biomarker is a soluble biomarker. In an embodiment, the biomarker is a serum biomarker.

In an embodiment, the test biological sample and/or reference biological sample is a biological fluid selected from blood or a faction thereof, urine, and amniotic fluid.

A person skilled in the art is familiar with the techniques for obtaining a serum sample. For example, a blood sample can be collected in serum separator vacutainer tubes (SSTs), centrifuged (e.g. at 3000 rotations per minute for 15 minutes), and stored at −80° C. Amniotic fluid (AF) samples can be obtained by amniocentesis from pregnant subjects. For example, samples can be centrifuged at 13,000×g for 10 minutes. The cell-free supernatants can be stored, (e.g. immediately at −80° C.) or tested for the level of a biomarker described herein. Reference samples can optionally be pooled together using for example equal total protein amounts, based on a total protein assay, such as a Bradford assay.

In an embodiment, the reference biological sample and test biological sample are the same tissue type, e.g. both comprise blood and/or serum. In an embodiment, the biological and/or reference sample is diluted. In an embodiment, the biological and/or reference sample is undiluted.

In certain embodiments, the samples are pre-processed prior to detecting the biomarker level. For example, a sample may be fractionated (e.g. by centrifugation or using a column for size exclusion), concentrated or proteolytically pre-processed such as trypsinized, depending on the assay or method of determining the level of biomarker employed.

In an embodiment, the assay or method described herein is performed on a test biological sample from a pregnant subject in the first trimester to provide a base-line level, and repeated on a second biological sample from the pregnant subject in the second trimester.

Current screening methods for Down syndrome or trisomy 21 incorporate physical markers with markers in maternal serum. The physical marker, fetal nuchal translucency (NT), is measured by ultrasound. Currently, the serum markers pregnancy-associated plasma protein A (PAPP-A) and human chorionic gonadotropin beta (β-hCG) are measured in maternal serum during the first trimester, and alpha fetoprotein (AFP), unconjugated estriol (uE3), β-hCG and inhibin A are measured in maternal serum during the second trimester. Accordingly, screening for these physical markers and serum markers in combination with the biomarkers disclosed herein can also be useful for screening for risk of Down syndrome in a fetus.

Thus, an embodiment of the disclosure includes the assay or method described herein further comprising determining the level of at least one biomarker selected from PAPP-A, β-hCG, AFP, uE3 and inhibin A polypeptides in a test biological sample. In another embodiment, the at least one biomarker is selected from PAPP-A and β-hCG polypeptides and the assay or method described herein is performed on a test biological sample from a pregnant subject in the first trimester. In yet another embodiment, the at least one biomarker is selected from AFP, uE3, inhibin A and the assay or method described herein is performed on a test biological sample from a pregnant subject in the second trimester. In yet another embodiment, the assay or method described herein further comprises determining the level of PAPP-A and β-hCG polypeptides in a test biological sample in the first trimester and the level of AFP, uE3, and inhibin A polypeptides in a test biological sample in the second trimester. In an embodiment, the blood is maternal blood. In another embodiment, the blood fraction is plasma or serum. In a further embodiment, the blood fraction is maternal plasma or serum. In still another embodiment, the method described herein further comprises using ultrasound to measure fetal nuchal translucency.

In another embodiment, at least one biomarker is selected from MUC13, CPA1 and CEL and at least one biomarker is selected from AFP and β-hCG. In a further embodiment, the biomarkers selected are MUC13 and AFP, MUC13 and β-hCG, and/or CPA1 and AFP.

A person skilled in the art will appreciate that a number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunopercipitation, immunohistochemistry, immunofluorescence, radioimmunoassay, dot blotting, and FACS. Accordingly, in an embodiment, determining the level of the at least one biomarker comprises using an immunoassay and/or mass spectrometric methods. In an embodiment, the mass spectrometric methods are selected from MS, MS/MS, LC-MS/MS, SRM, PIM, and other such methods that are known in the art. In another embodiment, LC-MS/MS further comprises 1D LC-MS/MS or 2D LC-MS/MS. In yet another embodiment, the immunoassay is selected from Western blot, ELISA, immunopercipitation, immunohistochemistry, immunofluorescence, radioimmunoassay, dot blotting, and FACS. In certain embodiments, the immunoassay is an ELISA. In yet a further embodiment, the ELISA is a sandwich type ELISA.

A person skilled in the art would know that a suitable antibody for determining the level of a biomarker that is a transmembrane protein includes an antibody directed to the extracellular portion of the protein.

The level of two or more markers can be determined for example using mass spectrometry-based assays such as single or multiple reaction monitoring assays. An example of such an assay is the "Product-ion monitoring" PIM assay. This assay is a hybrid assay wherein an antibody for a biomarker is used to extract and purify the biomarker from a sample e.g. a biological fluid, the biomarker is then trypsinized in a microtitre well and a proteolytic peptide is monitored with a triple-quadrapole mass spectrometer, during peptide fragmentation in the collision cell. More technical details can be found in Kulasingam V, Smith C R, Batruch I, Buckler A, Jeffery D A, Diamandis E P (2008) "Product ion monitoring" assay for prostate-specific antigen in serum using a linear ion-trap. *J of Proteome Res* 7: 640-647. Biomarker levels for a model biomarker has been quantified as low as 0.1 ng/mL with CVs less than 20%. Another example of multiple reaction monitoring assays is selected reaction monitory (SRM) assays. This assay is a based on triple quadrupole mass spectrometry and is one of the most versatile quantitation techniques, since it allows for relative (label-free) and absolute quantitation of multiple proteins simultaneously. Analytes present are quantified at relatively higher concentration in a biological fluid such as serum (e.g. ≥100 ng/mL) without antibody enrichment. In this case, the biological fluid (e.g. serum) is digested with trypsin and selected proteotypic peptides are monitored for various transitions during fragmentation, as described above. With such assays, multiplexing 5 or more biomarkers is possible. For example, test biological samples and reference biological samples may be prepared and SRM may be carried out as described in Example 1.

In an embodiment, antibodies or antibody fragments are used to determine the level of polypeptide or fragments thereof of one or more biomarkers of the disclosure. In an embodiment, the antibody or antibody fragment is labeled with a detectable marker. In a further embodiment, the antibody or antibody fragment is, or is derived from, a monoclonal antibody. A person skilled in the art will be familiar with the procedure for determining the level of a biomarker by using said antibodies or antibody fragments, for example, by contacting the sample from the subject with an antibody or antibody fragment labeled with a detectable marker, wherein said antibody or antibody fragment forms a complex with the biomarker.

The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the level of biomarkers of the disclosure is detectable indirectly. For example, a secondary antibody that is specific for a primary antibody that is in turn specific for a biomarker of the disclosure wherein the secondary antibody contains a detectable label can be used to detect the target polypeptide biomarker.

In certain embodiments, for example, when using Western blot analysis, the level of the biomarker can be normalized to an internal assay control such as an internal control. For example, the level of a biomarker may be normalized to an internal normalization control such as a polypeptide that is present in the sample type being assayed, for example a house keeping gene protein, such as beta-actin, glyceraldehyde-3-phosphate dehydrogenase, or beta-tubulin, or total protein, e.g. any level which is relatively constant between subjects for a given volume.

In an embodiment, the comparing the level of the at least one biomarker in a test biological sample with a corresponding reference biomarker polypeptide level comprises calculating the relative biomarker polypeptide level in a test biological sample compared to the reference biomarker polypeptide level. For example, the relative level of each of the at least one biomarker selected from MUC13, CEL, DPP4, CPA1, APP and TNC-C polypeptides in a test biological sample from a pregnant subject is compared to a corresponding reference biomarker polypeptide level or predetermined value and the relative change is calculated. In another embodiment, the absolute biomarker level is compared. Whether using a relative or absolute amount for example, a decreased level of MUC13, CEL, DPP4, and/or CPA1 polypeptide and/or an increased level of APP and/or TNC-C polypeptide in the test biological sample compared to a corresponding reference biomarker polypeptide level indicates an increased risk of Down syndrome and/or trisomy 21 in the fetus.

In an embodiment, the at least one biomarker comprises MUC13 or human MUC13, and the level of MUC13 in the test biological sample relative to the reference biomarker polypeptide level is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.2, 4.4, 4.6, 4.8, 5.0, 5.5, 6.0, 6.5, 7.0, 7.5, 8.0, 8.5, 9.0, 9.5, 10, 12, or 15 fold decreased. In an embodiment, the level of MUC13 in the test biological sample relative to the reference biomarker polypeptide level is at least about 1.7 fold decreased.

In an embodiment, the at least one biomarker comprises MUC 13 or human MUC13, and the level of MUC13 in the test biological sample (e.g. an undiluted serum sample) is at least 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1.0 ng/mL, 1.1 ng/mL, 1.2 ng/mL, 1.3 ng/mL, 1.4 ng/mL, 1.5 ng/mL, 1.6 ng/mL, 1.7 ng/mL, 1.8 ng/mL, 1.9 ng/mL, 2.0 ng/mL, 2.1 ng/mL, 2.2 ng/mL, 2.3 ng/mL, 2.4 ng/mL, 2.5 ng/mL, 2.6 ng/mL, 2.7 ng/mL, 2.8 ng/mL, 2.9 ng/mL, 3.0 ng/mL, 3.1 ng/mL, 3.2 ng/mL, 3.3 ng/mL, 3.4 ng/mL, 3.5 ng/mL, 3.6 ng/mL, 3.7 ng/mL, 3.8 ng/mL, 3.9 ng/mL, 4.0 ng/mL, 4.5 ng/mL, 5.0 ng/mL, 5.5 ng/mL or 6.0 ng/mL. In an embodiment, the test biomarker polypeptide level of MUC13 in the test biological sample is about 0.5 to about 3.0 ng/mL.

In an embodiment, the at least one biomarker comprises MUC 13 or human MUC13, and the reference biomarker polypeptide level of MUC13 in the reference biological sample is at least 1.4 ng/mL, 1.5 ng/mL, 1.6 ng/mL, 1.7 ng/mL, 1.8 ng/mL, 1.9 ng/mL, 2.0 ng/mL, 2.1 ng/mL, 2.2 ng/mL, 2.3 ng/mL, 2.4 ng/mL, 2.5 ng/mL, 2.6 ng/mL, 2.7 ng/mL, 2.8 ng/mL, 2.9 ng/mL, 3.0 ng/mL, 3.2 ng/mL, 3.4 ng/mL, 3.6 ng/mL, 3.8 ng/mL, 4.0 ng/mL, 4.2 ng/mL, 4.4 ng/mL, 4.5 ng/mL, 5.0 ng/mL, 5.5 ng/mL, 6.0 ng/mL, 6.5 ng/mL, 7.0 ng/mL, 7.5 ng/mL, 8.0 ng/mL, 8.5 ng/mL, 9.0 ng/mL, or 10 ng/mL. In an embodiment, the reference biomarker polypeptide level of MUC13 in the reference biological sample is about 1.2 to about 7 ng/mL, preferably about 3.0 to about 6.0 ng/mL.

In an embodiment, the at least one biomarker comprises APP or human APP, and the level of APP in the test biological sample relative to the reference biomarker polypeptide level is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4.0, 4.5, 5.0, 5.5, 6.0, 6.5, 7.0, 7.5, 8.0, or 9.0 fold increased. In an embodiment, the test biological sample relative to the reference biomarker polypeptide level is at least 1.9 fold increased.

In an embodiment, the at least one biomarker comprises APP or human APP, and the level of APP in the test biological sample is at least 1000 ng/mL, 1100 ng/mL, 1150 ng/mL, 1200 ng/mL, 1250 ng/mL, 1300 ng/mL, 1350 ng/mL, 1370 ng/mL, or 1390 ng/mL. In an embodiment, the test biological sample is at least about 1180 ng/mL to about 1320 ng/mL.

In an embodiment, the at least one biomarker comprises APP or human APP, and the level of APP in the reference biological sample is at least 435 ng/mL, 450 ng/mL, 455 ng/mL, 475 ng/mL, 500 ng/mL, 525 ng/mL, 550 ng/mL, 575 ng/mL, 600 ng/mL, 625 ng/mL, 650 ng/mL, 675 ng/mL, 700 ng/mL, 725 ng/mL, 750 ng/mL, 800 ng/mL, 850 ng/mL, 900 ng/mL, 950 ng/mL, 1000 ng/mL, 1050 ng/mL, or 1100 ng/mL. In an embodiment, the reference biological sample is at least about 435 ng/mL to about 700 ng/mL.

In an embodiment, the at least one biomarker comprises CEL or human CEL, and the level of CEL in the test biological sample relative to the reference biomarker polypeptide level is at leas about 1.2, 1.5, 2.0, 3.0, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.8, 6.9, 7.0, 10, 15, 20 or 30 fold decreased. In an embodiment, the level of CEL in the test biological sample relative to the reference biomarker polypeptide level is at least about 4 fold decreased.

In an embodiment, the at least one biomarker comprises DPP4 or human DPP4, and the level of DPP4 in the test biological sample relative to the reference biomarker polypeptide level is at least 1.2, 1.4, 1.6, 1.8, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6.0, 6.5, 7.0, 8.0, 9.0, 10, or 15 fold decreased. In an embodiment, the level of DPP4 in the test biological sample relative to the reference biomarker polypeptide level is at least about 2 fold decreased.

In an embodiment, the at least one biomarker comprises CPA1 or human CPA1, and the level of CPA1 in the test biological sample relative to the reference biomarker polypeptide level is at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.2, 5.4, 5.6, 5.8, 6.0, 6.5, 7.0, 8.0 or 10 fold decreased. In an embodiment, the level of CPA1 in the test biological sample relative to the reference biomarker polypeptide level is at least about 2 fold decreased.

In an embodiment, the at least one biomarker comprises TNC-C or human TNC-C, and the level of TNC-C in the test biological sample relative to the reference biomarker polypeptide level is at least 1.3, 1.5, 1.7, 1.9, 2.1, 2.3, 2.5, 2.7, 2.8, 2.9, 3.0, 3.1, 3.2, 3.3, 3.4, 3.5, 3.6, 3.7, 3.8, 3.9, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 10, 12, 14 or 16 fold increased. In an embodiment, the test biological sample relative to the reference biomarker polypeptide level is at least about 3.0 fold increased.

In an embodiment, the at least one biomarker comprises TNC-C or human TNC-C, and the level of TNC-C in the test biological sample is at least 230 ng/mL, 250 ng/mL, 300 ng/mL, 350 ng/mL, 400 ng/mL, 450 ng/mL, 500 ng/mL, 550 ng/mL, 600 ng/mL, 650 ng/mL, 675 ng/mL, 700 ng/mL, 750 ng/mL, 775 ng/mL, 800 ng/mL, 825 ng/mL, 850 ng/mL, 875 ng/mL, 900 ng/mL, 950 ng/mL, 1000 ng/mL, 1050 ng/mL, 1100 ng/mL, 1150 ng/mL, 1200 ng/mL, 1250 ng/mL, 1300 ng/mL, 1400 ng/mL, 1500 ng/mL or 1600 ng/mL. In an embodiment, the level of TNC-C in the test biological sample is about 500 ng/mL to about 875 ng/mL.

In an embodiment, the at least one biomarker comprises TNC-C or human TNC-C, and the level of TNC-C in the reference biological sample is at least 70 ng/mL, 90 ng/mL, 110 ng/mL, 130 ng/mL, 150 ng/mL, 170 ng/mL, 180 ng/mL, 185 ng/mL, 190 ng/mL, 195 ng/mL, 200 ng/mL, 205 ng/mL, 210 ng/mL, 215 ng/mL, 220 ng/mL, 225 ng/mL, 230 ng/mL, 235 ng/mL, 240 ng/mL, 245 ng/mL, 250 ng/mL, 255 ng/mL, 260 ng/mL, 265 ng/mL, 270 ng/mL, 275 ng/mL, 280 ng/mL, 285 ng/mL, 290 ng/mL, 295 ng/mL, 300 ng/mL, 325 ng/mL, 350 ng/mL 375 ng/mL 400 ng/mL, 450 ng/mL, 500 ng/mL, 550 ng/mL, or 600 ng/mL. In an embodiment, the level of TNC-C in the reference biological sample is about 185 ng/mL to about 275 ng/mL.

In an embodiment, the assays or methods described herein are repeated two or more times to determine if there is a reproducible difference in the level of at least one biomarker described herein in a test biological sample from a pregnant subject compared to the level of a corresponding reference biomarker polypeptide level, wherein a reproducible decreased level of MUC13, CEL, DPP4, and/or CPA1 polypeptide and/or a reproducible increased level of APP and/or TNC-C polypeptide in the test biological sample compared to a corresponding reference biomarker polypeptide level indicates an increased risk of Down syndrome or trisomy 21 in the fetus.

III. Compositions

A further aspect of the disclosure includes a composition comprising at least one biomarker specific detection agent, each of which binds a biomarker selected from MUC13, CEL, DPP4, CPA1, APP and TNC-C polypeptides and optionally a diluent. In an embodiment, the composition comprises at least two biomarker specific detection agents, each of which binds a biomarker selected from MUC13, CEL, DPP4, CPA1, APP and TNC-C polypeptides. In another embodiment, the composition comprises at least three, four, five or six biomarker specific detection agents, each of which binds a biomarker selected from MUC13, CEL, DPP4, CPA1, APP and TNC-C polypeptides. In certain embodiments, the composition comprises at least one biomarker specific detection agent which binds to the biomarker MUC13 polypeptide, optionally human MUC13 polypeptide. In another embodiment, the composition is for use in a assay or method described herein.

In an embodiment, the biomarker specific detection agent comprises an antibody or fragment thereof.

In an embodiment, the composition comprises a suitable carrier, diluent or additive as are known in the art. For example, wherein the detection agent comprises an antibody or fragment thereof, the suitable carrier can be a protein such as BSA.

In an embodiment, the biomarker specific detection agent further comprises a detectable label. A person skilled in the art will appreciate that the detection agents can be labeled. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

V. Kits

Another aspect of the disclosure is a kit for determining the level of at least one biomarker selected from MUC13, CEL, DPP4, CPA1, APP and TNC-C polypeptides in a test biological sample.

In an embodiment, the disclosure includes a kit for screening for risk of Down syndrome and/or trisomy 21 in a fetus comprising:
a) a biomarker specific detection agent that specifically binds a biomarker selected from MUC13, CEL, DPP4, CPA1, APP and TNC-C polypeptides; and
b) one or more of: instructions for performing an assay or method described herein; one or more kit controls; sterile collection tubes; microtiter wells and wash solution.

In an embodiment, the kit comprises two biomarker specific detection agents, each specifically binding a biomarker selected from MUC13, CEL, DPP4, CPA1, APP and TNC-C polypeptides. In another embodiment, the kit comprises three, four, five or six biomarker specific detection agents, each specifically binding a biomarker selected from MUC13, CEL, DPP4, CPA1, APP and TNC-C polypeptides. In yet another embodiment, the kit comprises at least one biomarker specific detection agent that specifically binds to MUC13 polypeptide. In yet another embodiment, the kit comprises at least one biomarker specific detection agent that specifically binds to human MUC13 polypeptide. In an embodiment, the biomarker specific detection agent comprises an antibody or fragment thereof. In an embodiment, the biomarker specific detection agent is an antibody. In an embodiment, the antibody is a monoclonal antibody. In an embodiment, the antibody is a polyclonal antibody.

In another aspect, the disclosure includes a kit for screening for risk of Down syndrome or trisomy 21 in a fetus comprising:
 a) an antibody that specifically binds a biomarker selected from MUC13; and
 b) one or more of instructions for performing an assay or method described herein; one or more kit controls; sterile collection tubes; microtiter wells and wash solution.

In an embodiment, the kit comprises two, three, four, five or six antibodies, each antibody specifically binding a biomarker selected from MUC13, CEL, DPP4, CPA1, APP and TNC-C polypeptides.

In an embodiment, the kit comprises an immunoassay for screening for risk of Down syndrome and/or trisomy 21 in a fetus comprising at least one capture antibody, optionally immobilized on a solid support, wherein each capture antibody selectively binds a biomarker selected from MUC13, CEL, DPP4, CPA1, APP and TNC-C polypeptides. In an embodiment, the immunoassay further comprises a detection antibody directed for each biomarker recognized by a capture antibody. In an embodiment, the detection antibody is labeled, for example fluorescently labeled and/or labeled with an enzyme such as horseradish peroxidase, or any label described herein. In an embodiment, the immunoassay is an ELISA. In an embodiment, the immunoassay is a multiplex assay. In another embodiment, the immunoassay comprises at least 2, 3, 4, 5, or 6 capture antibodies and in another embodiment at least 2, 3, 4, 5, or 6 detection antibodies. In still another embodiment, the immunoassay comprises at least one capture antibody that selectively binds the biomarker MUC13 polypeptide. In another embodiment, the immunoassay comprises at least one capture antibody that selectively binds the biomarker human MUC13 polypeptide.

In an embodiment, the kit further comprises a kit control. In an embodiment, wherein for example the kit is for a MRM/SRM assay, the kit control is optionally a quantity of a peptide fragment of a biomarker polypeptide that can for example be used to prepare a standard curve, for example serotransferrin (TF). In an embodiment, the kit control is a peptide of about 8 to about 20 amino acids, optionally SEQ ID NO:14, and/or prostate-specific antigen (KLK3), for example the peptide of SEQ ID NO:15. A person skilled in the art would understand that any peptide can be used in the control. In an embodiment, the kit control is a recombinant polypeptide of the analyte (e.g. biomarker to which the kit is directed). For example, in an embodiment, the recombinant polypeptide is a MUC13 polypeptide (e.g. minimally comprising the epitope recognized by the detection agent). In another embodiment, the kit control is selected from CEL, DPP4, CPA1, APP and TNC-C recombinant polypeptide (e.g. minimally comprising the epitope recognized by the detection agent). In an embodiment, the kit control is a serum sample or other fluid comprising a known concentration of the analyte, for example MUC1 recombinant polypeptide and/or selected from CEL, DPP4, CPA1, APP and TNC-C recombinant polypeptide (e.g. minimally comprising the epitope recognized by the detection agent). In another embodiment, wherein the kit is for detecting polypeptide levels by an immunohistochemical assay, the kit control can comprise an antibody control, useful for example for detecting non-specific binding and/or is a quantity of protein (e.g. BSA) for standardizing the amount of protein in the sample. The kit control is in another embodiment a control serum sample corresponding for example to a non-pregnant subject, or corresponding to a subject pregnant with a trisomy-21 affected (e.g. positive control) or unaffected fetus (e.g. negative control).

The following non-limiting examples are illustrative of the present disclosure:

EXAMPLES

Example 1

Prenatal screening test for Down syndrome (DS) can be improved by discovery of novel biomarkers. A multiplex Selected Reaction Monitoring (SRM) assay was developed to test previously identified thirteen candidate proteins in amniotic fluid (AF). One unique peptide was selected for each protein based on discovery data, while three MS/MS transitions were selected based on intelligent SRM results. For one of the candidates, matrix metalloproteinase-2 (MMP2), ELISA was also performed to validate SRM results in AF and to test serum samples. Comparison of AF samples from DS versus controls via SRM assay revealed five proteins that were differentially expressed. Bile salt-activated lipase, mucin-13, carboxypeptidase A1, and dipeptidyl peptidase 4 showed a decrease in DS-affected AF, and MMP2 showed an increase, in comparison to controls ($P<0.05$). Discovery-based spectral counting ratios and SRM ratios showed a strong correlation, and MMP2 ELISA further confirmed the validity of the SRM data. Potential implications of differentially expressed proteins during fetal development are proposed. Our data also shows that SRM can provide a high-throughput and accurate platform for biomarker verification.

Down syndrome, also known as Trisomy 21, is caused by complete or partial triplication of human chromosome 21 (HSA21), which is the smallest autosome with a length of 47 megabases. Down syndrome is the most common chromosomal anomaly in humans, and it also constitutes the most common congenital cause of intellectual disability in live-born infants. Currently, Down syndrome prevalence is roughly 1 in 750 live births (1). This rate, however, underestimates the true incidence since it does not include induced and spontaneous abortions (2). The currently available screening tests for DS perform risk calculation, mostly based on measurements of biochemical markers from maternal serum, resulting in 85-95% detection rate (3). Due to the uncertainties associated with the current screening, invasive diagnostic procedures such as amniocentesis are frequently used, although only a small fraction (1-5%) of the tested individuals actually have an affected fetus (4, 5). To further reduce or even eliminate unnecessary invasive procedures, it is important to advance the current screening tests by discovering additional biomarkers to improve the predictive power and specificity.

Amniotic fluid (AF), among all biological fluids, has two major advantages over plasma as a reservoir of biomarkers for Down syndrome detection. First, it contains the greatest concentration of fetal and pregnancy-related proteins. AF before skin keratinization of the fetus is especially similar to fetal plasma in composition. Secondly, the complexity of AF poses less challenge for proteomic analysis compared to that of plasma or serum. Therefore, AF has been proteomically studied in depth to explore its potential as a medium for biomarker discovery (6-8). Furthermore, several studies have attempted to compare AF proteins from chromosomally normal (CN) and DS-affected pregnancies semi-quantitatively and quantitatively (9-11). A comparison of spectral counts of proteins from unaffected and affected (Down syndrome) AF proteome revealed 60 candidates. Since spectral counts endow only semi-quantitative comparisons, candidates revealed through spectral counts must be confirmed by more accurate and sensitive assays (9). Previously, two candidates among the 60 proposed candidates that showed differential expression in AF, amyloid precursor protein and tenascin-C, were confirmed by ELISA. However, many other candidates could not be readily confirmed or verified due to lack of sensitive assays or specific antibodies.

Recent improvements in mass spectrometry-based quantitative technologies provides alternative quantitation tools even in complex biological samples. Selective reaction monitoring (SRM) based on triple quadrupole mass spectrometry is one of the most versatile label-free quantitation techniques, since it allows for relative and absolute quantitation of multiple proteins simultaneously. SRM assays provide not only high selectivity and sensitivity, but also a more feasible and automated means to verify putative biomarkers for which traditional immunoassays are unavailable. Moreover, SRM offers a unique set of advantages. For example, SRM allows differentiation of protein and peptide isoforms as long as they present unique sequences. This advantage becomes especially important when analyzing complex biological mixtures, such as AF and serum, which contain numerous proteins that may cross-react in immunoassays without the optimal specificity. Another advantage is that SRM allows high throughput quantitation for multiple proteins in a single experiment. For example, Whiteaker et al monitored over 80 proteins in plasma by SRM, reporting detection of many proteins at the concentration of 0.5 fmol/μL in plasma (12). Finally, improvements in SRM technology have been substantial for the past several years. The methodologies are rapidly becoming more refined with introduction of more powerful mass spectrometers, more sophisticated analysis tools and software, and introduction of stable isotope-labeled standards for absolute quantification.

A mass spectrometry-based SRM assay was developed to assess the differential expression of thirteen candidate proteins in AF in order to verify the discovery data. Relative quantitation in 18 individual AF samples from unaffected and Down syndrome-affected pregnancies was performed. The multiplex SRM assay was developed based on the fragmentation information obtained through experimental outputs from our previous LC-MS/MS study, and it targeted one unique peptide for each of the thirteen candidate proteins (Table 1). This presents the first SRM study to assess candidate biomarkers for detection of Down syndrome in 18 clinical (amniotic fluid) samples.

Materials and Methods
2.1 Sample Collection

Amniotic fluid (AF) samples were obtained from pregnant women at 16-20$^{th}$ week gestation who underwent amniocentesis at the second trimester of pregnancy. Samples were collected with written consent and ethics board approval. A previous semi-quantitation study used pooled AF samples by combining equal amount of proteins from each individual sample (9). This study used the original set of AF samples which have been separately aliquoted and stored at −80° C. for verification studies. AF samples fell into two groups: chromosomally normal controls (n=9) and Down syndrome group (n=9). Samples were matched in terms of gestational age and gender of the fetus. Each sample was stored after centrifuging at 13,000×g for 10 min to eliminate any cellular debris.

2.2 Sample Preparation

Before analysis, the samples were thawed at 4° C. and centrifuged once more at 13,000×g for 10 min. Total protein for each AF sample was measured by a Bradford assay (Pierce, USA), and the volume was adjusted to extract equal amounts of total protein from the individual samples. AF proteins (30 μg) were denatured with 0.1% Rapigest (Waters, Milford, Mass., USA) at 60° C., and the disulfide bonds were reduced with 10 mM dithiothreitol (Sigma-Aldrich, St. Louis, Mo., USA) before being subject to alkylation with 20 mM iodoacetamide. Samples were then digested with sequencing grade modified trypsin (Promega, Madison, Wis., USA) overnight at 37° C. Ninety-six femtomoles of heavy $^{13}C6$, $^{15}N2$ L-Lysine-labeled peptide (LSEPAELTDAVK* (SEQ ID NO:15)) of KLK3 protein was added as a relative internal standard peptide for the SRM runs. Rapigest was cleaved with 1% trifluoroacetic acid, and all samples were centrifuged at 4000×g for 10 min. Peptides were purified and extracted using 10 μL OMIX C18 tips (Varian, Lake Forest, Calif., USA), and were eluted using 5 μL 65% acetonitrile solution (0.1% formic acid, 0.02% trifluoacetic acid). The final sample was diluted to 130 μL to yield three replicates of 40 μL.

2.3 Peptide Selection for SRM

A total of 13 candidate proteins were selected out of the 60 candidates reported previously (9). From this list, the number of candidates was further reduced based on their relative abundance in AF. Mid- to high-abundance proteins were preferred over low-abundance proteins, and the selection was based on the number of target protein peptides that showed high frequencies in an MS scan. Also, proteins that were quantified based on unique peptides, via spectral counting previously, were preferred. Proteotypic peptide for each candidate was manually selected based on identification data acquired using an LTQ-Orbitrap instrument.

Several criteria were applied to select candidate peptides: display of multiple spectra and clear y-ion fragmentation, peptide length of 8 to 20 amino acids, and preferably absence of modifications at cysteine, methione, and tryptophan. Additionally, any non-unique peptides were removed after the sequence search result obtained via the Basic Local Alignment Search Tool (BLAST). When more than one peptide from a single protein qualified for all the criteria, a peptide that yielded less significant overlap of time interval with other peptides was preferred. In silico digestion and fragmentation of each peptide was performed with Pinpoint software (Thermo Scientific, USA).

2.4 SRM and iSRM Conditions

Tryptic peptides were loaded onto a 2 cm $C_{18}$ column (inner diameter: 150 μm) and were eluted to a resolving 5 cm analytical $C_{18}$ column with a 15 μm tip (inner diameter: 75 μm) for separation (New Objective). This setup was online-coupled to a triple-quadrupole mass spectrometer (TSQ Quantum Ultra, Thermo Scientific) using a nanoelectrospray ionization source (nano-ESI, Proxeon A/S). The details of liquid chromatography and MS methods can be found in a previous study (13). Briefly, a 60-min, three-step gradient was used to load peptides onto the column via an EASY-nLC pump (Proxeon A/S). Running buffer contained 0.1% (v/v) formic acid in water, and elution buffer contained 0.1% (v/v) formic acid in acetonitrile. Peptides were analyzed by SRM methods using the following parameters: predicted collision energy values, 0.002 m/z scan width, 10 ms scan time, 0.2 resolution at the first quadrupole, 0.7 resolution at the third quadrupole, 1.5 mTorr pressure at the second quadrupole, tuned tube lens values, 7 V skimmer offset. The identity of each peptide was confirmed by performing intelligent SRM (iSRM). This method targeted peptides in 3-min scheduled acquisition windows, monitoring for two primary transitions for each peptide. Once the intensity of the two transitions overcame the threshold of 300, this triggered the program to acquire the intensity of six additional transitions for the same peptide.

2.5 Optimization of the SRM Assay and Data Analysis

The three most intense and reproducible transitions for each peptide from iSRM results were selected to develop the final SRM method. One of the unique and abundant peptides of serotransferrin (TF), a high-abundance protein in AF, was selected to serve as an additional relative internal standard. Being one of the most abundant proteins in AF, it was hypothesized that TF abundance would not significantly differ between AF samples. Therefore, TF relative amounts were measured to be used as an additional indication that protein digestion and the whole sample preparation protocol were similarly efficient across all individual samples. In total, the final method targeted 45 transitions of 15 peptides (13 candidates, TF and the internal standard). The method included a 60-min gradient within a 84-min method, and the detection window for transitions were scheduled with approximately 2-min intervals within the 60-min gradient. Raw output files for each sample were manually analyzed using LCquan software (version 2.5.6) to verify peak areas used for quantification (FIG. 1). Quantification was executed after normalization against an internal standard peptide (KLK3*) to offset technical errors.

2.6 Quantification of MMP2 by Enzyme-Linked Immunosorbent Assay (ELISA)

The concentration of MMP2 was measured using sandwich ELISA with a Human MMP-2 Quantikine Kit (R&D Systems). A total of 18 AF (n=9 each for DS and CN-AF) and 71 maternal sera (n=22 for DS; n=49 for CN) samples were measured. A 10-fold dilution was prepared for both AF and serum samples, and ELISA was performed according to the instructions provided with the kit. The results were analyzed using SPSS and GraphPAD Prism (GraphPAD Software). All statistical analyses were performed via independent samples t-test using SPSS software (version 17.0). P values of <0.05 were considered significant.

Results and Discussion

Previously, 60 candidate proteins that were differentially expressed in DS-affected AF, compared to the controls, were identified by semi-quantitative spectral counting (9). Out of the 60 candidate proteins, the target proteins were selected based on their relative abundance, estimated by the frequency of MS1 spectra. Low-abundance proteins were omitted since they are less likely to be accurately quantified with SRM assay in the unfractionated or non-enriched digests of AF. As a result, an SRM assay was developed targeting a total of 13 candidate proteins in addition to two internal standards, for quantification and comparison between the DS and unaffected groups (Table 1). In order to obtain reliable quantification via SRM assays, it is essential to execute sample preparation precisely and to assess the reproducibility of the assay. Thus, three independent SRM runs per each sample were performed to monitor the reproducibility.

TABLE 1

Top three transitions selected based on iSRM data for each peptide (precursor ion) and their retention time.

| Gene Name | Precursor Ion (m/z) | Top Three Transitions (m/z) | Retention Time (min) |
|---|---|---|---|
| CA1 | 485.800 | 459.292 | 12.4 |
| | | 572.376 | |
| | | 758.440 | |
| TF | 489.748 | 464.286 | 7.9 |
| | | 563.355 | |
| | | 735.403 | |
| CPA1 | 594.316 | 573.335 | 5.7 |
| | | 888.442 | |
| | | 987.510 | |
| CEL | 638.861 | 880.441 | 24.3 |
| | | 993.525 | |
| | | 1163.63 | |
| KLK3 (spiked-in internal standard) | 640.848 | 654.391 | 9.9 |
| | | 951.523 | |
| | | 1080.566 | |
| CTGF | 706.834 | 652.341 | 13.1 |
| | | 799.409 | |
| | | 912.493 | |
| COMP | 743.878 | 630.356 | 8.0 |
| | | 701.394 | |
| | | 886.474 | |
| FBN2 | 750.359 | 909.406 | 10.5 |
| | | 1124.496 | |
| | | 1237.580 | |
| DPP4 | 755.827 | 869.399 | 11.5 |
| | | 1032.463 | |
| | | 1195.526 | |
| MUC13 | 808.899 | 894.467 | 18.1 |
| | | 1007.551 | |
| | | 1154.620 | |
| AHSG | 830.885 | 923.465 | 11.8 |
| | | 1095.513 | |
| | | 1224.556 | |
| IGFBP5 | 879.932 | 915.496 | 16.7 |
| | | 1099.581 | |
| | | 1196.634 | |
| NPC2 | 922.437 | 732.370 | 7.2 |
| | | 1058.529 | |
| | | 1315.613 | |
| MMP2 | 1054.512 | 694.315 | 19.6 |
| | | 1120.526 | |
| | | 1235.553 | |
| ADAMTS1 | 1157.099 | 630.320 | 30.8 |
| | | 840.457 | |
| | | 968.515 | |

In order to select SRM transitions, two complementary approaches were used. First, the previous LC-MS/MS data obtained from LTQ-Orbitrap was manually analyzed using Scaffold software to obtain experimental spectral information including the transitions for the peptides of interest. All selected precursor ions had charge state of 2 to 3. The peptide ions that display modifications were selected against, if such modifications constitute greater than 5% but less than 95% of the observed spectra, to ensure accurate quantification. Up to eight experimentally observed transitions were compared to the discovery MS/MS spectrum for evaluation. Secondly, Pinpoint software (Thermo Scientific, USA) was used to refine the list of transitions. Pinpoint generates the most abundant precursor and product ions for comparison, as well as automated optimal collision energies for SRM transitions. The MS/MS spectra of the precursor ions were examined to ensure selection of the fragment ions with the highest intensities. Fragment ions that displayed the highest and second-highest MS/MS intensities from experimental data were selected as primary ions for iSRM method.

The peak area for each of the three transition of the target proteins were extracted from the spectrum of each sample via LCquan. Each peak area was manually inspected on LCquan for consistent peak integration to obtain accurate AUC. The area under the curve (AUC) for each peptide ion was then normalized to the AUC of the KLK3 standard peptide to offset technical variations between the SRM runs. Thirteen candidates and TF were then assessed by comparing the mean values in DS and control groups. First, relative abundances for TF were used to evaluate the global performance of the SRM assay. Technical variation was estimated based on CVs for triplicate injections of the same sample. Technical variation was found to be 25% or less (8% on average) for all 18 samples. Biological variation was estimated based on CVs of relative abundances of 9 samples within groups of normal and DS samples. Such variations were found to be 56% and 48% on average, respectively (excluding carbonic anhydrase 1 which had a few exceptional outliers). Finally, the ratio of mean values for TF was found 1.1, supporting the initial assumption about similar abundances of TF in individual AF samples. Based on these observations, the sample preparation protocol and SRM assay are reproducible enough to enable comparison of relative abundances for chosen candidate biomarkers.

Figure 2:
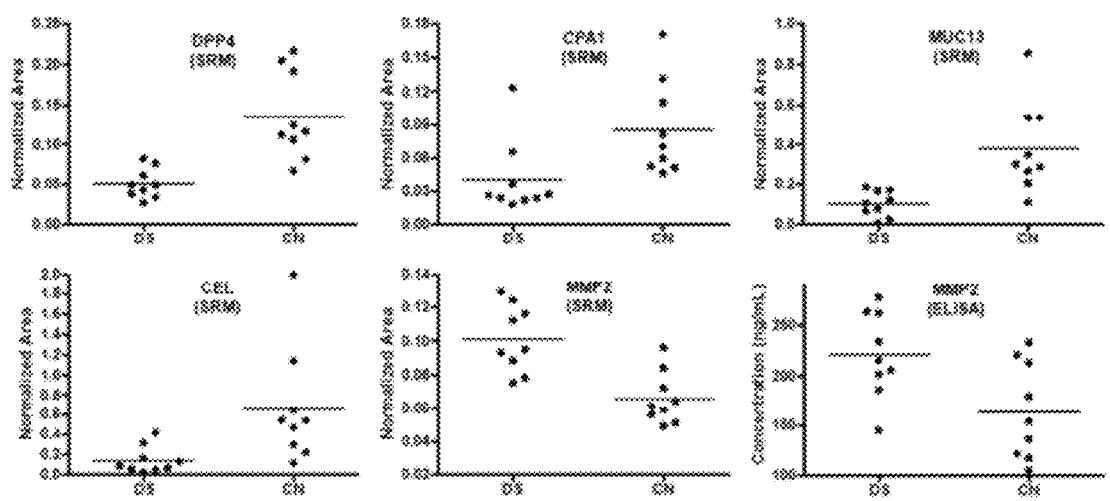
FIG. 2. Measurement of DPP4, CPA1, MUC13, CEL, and MMP2 in amniotic fluid samples from Down syndrome-affected (DS) and chromosomally-normal (CN) pregnancies. Note the decreases in DPP4, CPA1, MUC13, and CEL, and the increase in MMP2 in amniotic fluid of Down syndrome fetuses (P<0.05). MMP2 was also measured by ELISA. (DS=Down syndrome; CN=Chromosomally Normal controls).
Figure 3:
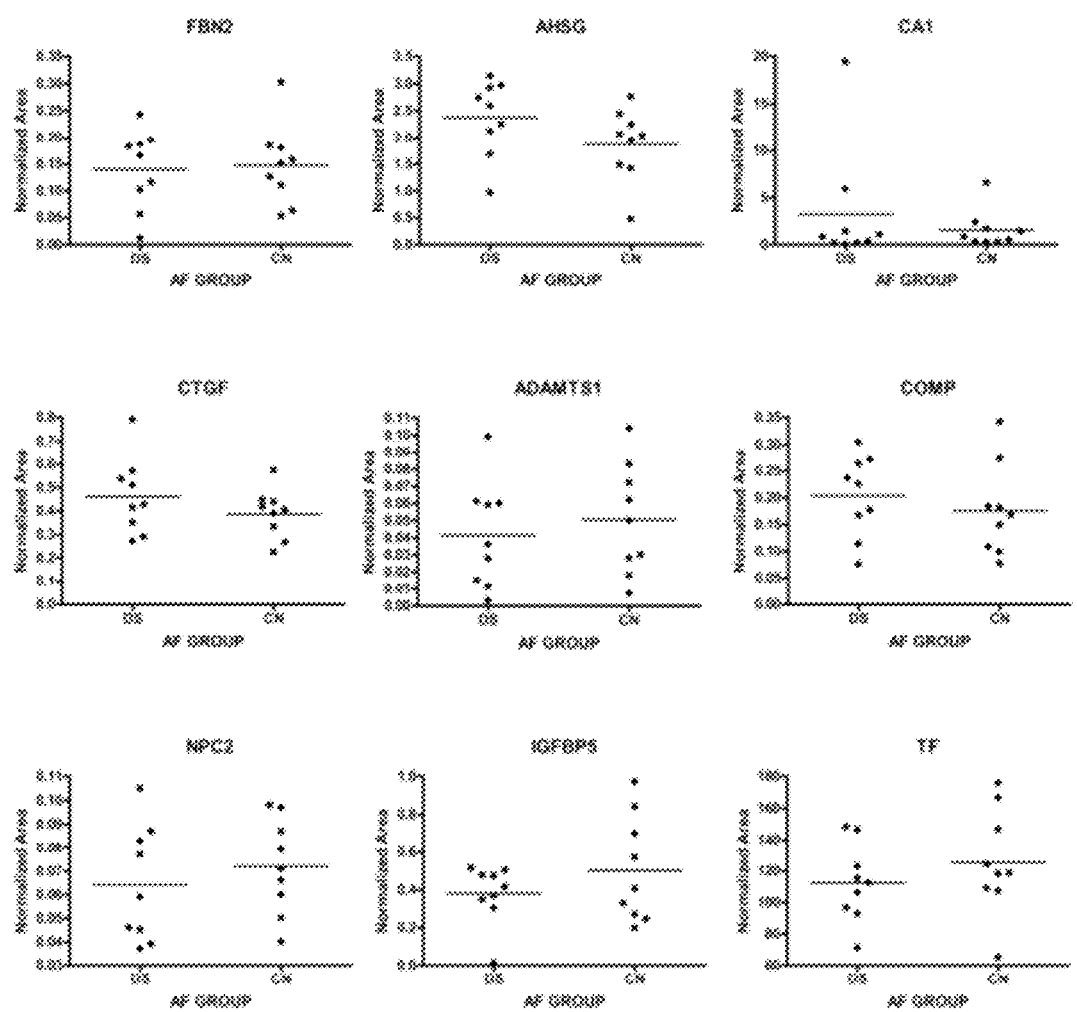
FIG. 3. SRM assays for eight tested proteins in DS-AF samples.

Of the 13 candidates, 5 proteins exhibited a statistically significant modulation in individual DS samples ($P<0.05$) (FIG. 2). Bile salt-activated lipase (CEL), mucin-13 (MUC13), dipeptidyl peptidase 4 (DPP4), and carboxypeptidase A1 (CPA1) showed a decrease of 4.5-, 3.7-, 2.4- and 2.3-fold, respectively. Matrix metalloproteinase-2 (MMP2) showed a statistically significant difference in DS by 1.5-fold (Table 2). The rest of the candidates (insulin-like growth factor-binding protein 5, a disintegrin and metalloproteinase with thrombospondin motifs 1, epididymal secretory protein E1, alpha-2-HS-glycoprotein, fibrillin-2, cartilage oligometric matrix protein, connective tissue growth factor, carbonic anhydrase 1) did not show statistically significant increase or decrease in DS-AF compared to the controls (FIG. 3). The mean concentration of MMP2 in AF was 221 ng/mL in the DS group, and 164 ng/mL in the CN group (P=0.018). The DS/CN ratio from ELISA result was 1.35, which is close to the observed SRM ratio of 1.47 (FIG. 2). Unlike in AF, MMP2 levels in serum samples showed no significant difference between CN (183 ng/mL) and DS (203 ng/mL) groups.

TABLE 2

Quantification of candidate biomarkers for Down syndrome detection in amniotic fluid.

| Gene Name | Protein Name | Accession Number | Peptide | SEQ ID NO: | Parent ion (m/z) | SC[1] Ratio (DS/CN) | SRM Ratio[2] (DS/CN) | P-value[3] |
|---|---|---|---|---|---|---|---|---|
| CEL | Bile salt-activated lipase | P19835 IPI00099670 IPI00843810 IPI00218674 | LGLLGDSVDIFK | 1 | 638.86 | 0.00 | 0.22 | 0.029 |
| MUC13 | Mucin-13 | Q9H3R2 IPI00011448 | SSSSNFLNYDLTLR | 2 | 808.90 | 0.36 | 0.27 | 0.006 |
| DPP4 | Dipeptidyl peptidase 4 | P27487 IPI00018953 IPI100924974 IPI00927124 IPI00924746 | WEYYDSVYTER | 3 | 755.83 | 0.67 | 0.42 | 0.001 |
| CPA1 | Carboxypeptidase A1 | P15085 IPI00009823 | ISVADEAQVQK | 4 | 594.32 | 0.64 | 0.44 | 0.027 |
| MMP2 | Matrix metalloproteinase-2 | P08253 IPI0089585 IPI00027780 | IIGYTPDLDPETVDDAFAR | 5 | 1054.51 | 2.90 | 1.50 | 0.002 |
| IGFBP5 | Insulin-like growth factor-binding protein 5 | P24593 IPI00816014, IPI00816087, IPI00924537, IPI00029236 | ALSMC*PPSPLGC*ELVK | 6 | 879.93 | 0.82 | 0.77 | >0.05 |
| ADAMTS1 | A disintegrin and metalloproteinase with thrombospondin motifs 1 | Q9UHI8 IPI00442897, IPI00796841, IPI00005908 | GAFYLLGEAYFIQPLPAASER | 7 | 1157.10 | 0.29 | 0.91 | >0.05 |
| NPC2 | Epididymal secretory protein E1 | P61916 IPI00301579 | EVNVSPC*PTQPC*QLSK | 8 | 922.44 | 3.00 | 1.00 | >0.05 |
| AHSG | Alpha-2-HS-glycoprotein | P02765 IPI00022431, IPI00791521, IPI00792808, IPI00794559, IPI00795830 | EHAVEGDC*DFQLLK | 9 | 830.89 | 1.62 | 1.14 | >0.05 |
| FBN2 | Fibrillin-2 | P35556 IPI00019439 | YVISQGNDDSVFR | 10 | 750.36 | 1.79 | 1.11 | >0.05 |

TABLE 2-continued

Quantification of candidate biomarkers for Down syndrome detection in amniotic fluid.

| Gene Name | Protein Name | Accession Number | Peptide | SEQ ID NO: | Parent ion (m/z) | SC[1] Ratio (DS/CN) | SRM Ratio[2] (DS/CN) | P-value[3] |
|---|---|---|---|---|---|---|---|---|
| COMP | Cartilage oligomeric matrix protein | P49747 IPI00384067, IPI00643348, IPI00910249, IPI00028030 | ELQETNAALQDVR | 11 | 743.88 | 2.89 | 1.18 | >0.05 |
| CTGF | Connective tissue growth factor | P29279 IPI00020977, IPI00220647 | DGAPC*IFGGTVYR | 12 | 706.83 | 2.00 | 1.33 | >0.05 |
| CA1 | Carbonic anhydrase 1 | P00915 IPI00079827, IPI00796435, IPI00788926, IPI00215983 | VLDALQAIK | 13 | 485.80 | 5.14 | 2.44 | >0.05 |
| TF | Serotransferrin | A0PJA6 IPI00022463 | DGAGDVAFVK | 14 | 489.75 | 1.31 | 0.91 | >0.05 |
| KLK3[4] | Prostate-specific antigen | P07288 IPI00102806 | LSEPAELTDAVK [HeavyK] | 15 | 640.85 | | | >0.05 |

[1]Spectral counts from pooled samples reported previously (9).
[2]Ratio between means of each group (DS/CN; SRM values were derived by analysis of individual samples; n = 9 per group).
[3]P-values for difference in mean amount (normalized peak area) of each candidate from CN- and DS-AF by SRM.
[4]KLK3 heavy peptide injected as an internal standard.
*These cysteines have S-carbamidomethyl modification.

The Pearson's correlation coefficient that represents correlations between spectral counting ratios and SRM ratios for the candidates was 0.904 (P=0.01), supporting the initial rationale of candidate selection based on spectral counts from pooled samples. For example, carbonic anhydrase 1 and insulin-like growth factor-binding protein 5 initially showed a marked difference in both the spectral count and preliminary SRM results that were acquired from pooled samples. The subsequent SRM data for individual samples revealed few AF samples with prominently high concentrations of carbonic anhydrase 1 and insulin-like growth factor-binding 5. These samples affected the final concentration of both proteins in the pooled samples used for the initial selection of candidates based on spectral counting comparison. Thus, analysis of individual samples via SRM assay allowed for elimination of such artefacts.

The collective results from the previous and present study indicate that comparison of two conditions via spectral counting, if used thoughtfully, can be used as an effective strategy to select the initial list of candidates. In general, spectral counting is defined as the total number of spectra identified for a protein, and it has been widely used as a practical and rapid measure of relative protein abundance (14). For quantitative proteomics, the more complicated sample preparation steps are, the more sources of variability are introduced. Therefore, spectral counting provides semi-quantitative information acquired together with protein identification. Due to its inherent limitations, however, spectral counting should be considered as an initial sieve to identify potential candidates out of thousands of proteins in complex mixtures. Ideally, next step should involve a high-throughput quantitative technique to assess the quantification of dozens of potential candidates identified via spectral counting, since the list of candidates discovered via spectral counting may include some false candidates.

SRM, also known as multiple reaction monitoring (MRM), has long been utilized to quantitate small molecules such as hormones in biological samples. For the past decade, SRM has been explored and optimized for proteomic quantitation with the improvements of triple quadrupole mass spectrometers. Once optimized, SRM can offer an antibody-independent specific assay, and its multiplexing capability will yield cost-efficient means to analyze many target proteins simultaneously. Thus, coupling spectral counting with SRM would provide an effective and fast pipeline for biomarker discovery. Sensitivity of SRM assay, however, may be compromised due to the complexity of sample and the nature of candidate proteins. For example, unlike ELISA or other immunoassays, detection of low-abundance proteins (100 ng/mL or less) via SRM in the unfractionated digest of complex sample will not show consistency, for either qualitative or quantitative study, due to the current limitations of mass spectrometry. Efforts to improve sensitivity of SRM have focused on enrichment of target proteins by techniques such as depletion of high-abundance proteins and SISCAPA (15). This study aimed to confirm some of the candidates previously proposed based on the semi-quantitative spectral counting data. This is the first study to quantify proteins in amniotic fluid using SRM assays.

MMP2 levels were assessed in both individual AF and maternal serum samples, since a sensitive ELISA kit was commercially available for MMP2. Unlike in AF, MMP2 levels in serum samples showed no significant difference between CN and DS groups. This is likely due to abundance of MMP2 in serum, irrespective of pregnancy. MMP2 is a ubiquitously secreted or membraneous metalloproteinase found in fibroblasts, and it is involved in multiple processes such as angiogenesis, tissue repair, and inflammation, atherosclerotic plaque rupture, and valve pathology (16-18). The finding of increased (1.5-fold) levels of MMP2 in AF of DS fetuses may provide clues for explaining as to why most DS patients possess cardiovascular defects but have reduced risk for solid tumors and atherosclerotic plaque formation. Moreover, increased MMP2 activity has been linked to increased degradation of secreted amyloid-β (18), a key player of Alzheimer's disease (AD) (19). Recently, multiple MMPs were measured in blood and cerebrospinal fluid in Alzheimer's patients, and MMP-2 showed significant decrease in cerebrospinal fluid but not in blood of AD patients (20). Therefore, increases in amyloid precursor protein (9) together with increases in MMP2 during fetal development may be involved in the eventual pathogenesis of early-onset AD, which is prevalent among DS patients.

Nuchal translucency test, which measures the thickness of the skin fold behind the nape of the neck of a fetus, is often used for first-trimester screening of DS. In DS fetuses, such thickening may be attributed to lymphatic engorgement, although the molecular mechanism of this symptom is unknown (21). DDP4 is a cell surface glycoprotein receptor mainly expressed in lymphatic vessels (22), and studies have shown that DDP4 may be involved in the T-cell activation and lymphatic development (22,23). Hence, decreased DPP4 expression in fetus may be related to lymphatic maldevelopment in DS-affected individuals.

CEL is a secreted lipolytic protein that hydrolyzes cholesterol esters, triacylglycerols, and phospholipids, and it is mainly produced from the mammary gland and pancreas. Its dysregulated expression in macrophages has been linked to promotion of atherosclerosis, indicating its importance in lipid regulation (24). Interestingly, hypercholesterolemia and other types of lipid dysregulation have been reported in DS fetuses, and hypercholesterolemia has been proposed as a risk factor for dementia in AD (25,26). Therefore, it may be that the impact of reduced CEL expression on its immediate pathways leads to lipid dysregulation, contributing to the eventual dementia in DS-affected individuals.

MUC13 is a transmembrane protein that is highly expressed in epithelial tissues, particularly along gastrointestinal tracts (27). Little is known about the functions of MUC13 other that its involvement in barrier functions of epithelium. Abnormal expression of MUC13 has been linked to gastric, colon, and ovarian cancer, as well as ulcerative colitis (28-30). Further investigation on the functions and expression of MUC13 during fetal development will allow further understanding of its potential involvement in DS pathogenesis. Finally, CPA1 is a secreted protein that catalyzes the release of a C-terminal amino acid, but little is known about its biological function.

Traditional techniques for biomarker discovery include Western blotting, ELISA, or immunohistochemistry, and they all require suitable antibodies which often require ample time and cost for development. SRM analysis, therefore, allows an effective determination of which biomarkers are worth pursuing by developing appropriate antibodies. The above data also confirm that SRM can provide a high-throughput and accurate platform for biomarker verification, when immunoassays are unavailable. With continuous improvements, SRM may soon become a standard method for biomarker verification, replacing some of the immunoassays. The next step to this study would involve development of ELISA and performing clinical validation using a larger number of samples, both AF and serums.

In this study, previous discovery data for 13 candidate markers of DS in AF which were previously identified from a semi-quantitative study were verified. In addition, it was shown for the first time that five different proteins, which are not previously known biomarkers or related proteins of DS, are differentially expressed in AF. Proposed also is their potential involvement in DS phenotypes and pathology. As indicated by the case of MMP2, even if a biomarker may be informative in AF, its performance in maternal serum may be compromised, especially when the marker is not specific to pregnancy.

TABLE 3

Independent samples t-test for CPA1, DPP4, MUC13, MMP2, CEL, and TF measurements by SRM in chromosomally normal versus trisomy 21 amniotic fluid samples.

| | | t-test for Equality of Means | | | | | | |
|---|---|---|---|---|---|---|---|---|
| | | | | | | | 95% Confidence Interval of the Difference | |
| | | t | df | Sig. (2-tailed) | Mean Difference | Std. Error Difference | Lower | Upper |
| CPA1 | Equal variances assumed | −2.476 | 16 | .025 | −.050444 | .020377 | −.093641 | −.007248 |
| | Equal variances not assumed | −2.476 | 14.038 | .027 | −.050444 | .020377 | −.094137 | −.006752 |
| DPP4 | Equal variances assumed | −4.318 | 16 | .001 | −.071556 | .016573 | −.106689 | −.036422 |
| | Equal variances not assumed | −4.318 | 10.561 | .001 | −.071556 | .016573 | −.108219 | −.034892 |
| MUC13 | Equal variances assumed | −3.572 | 16 | .003 | −.278997 | .078101 | −.444564 | −.113429 |
| | Equal variances not assumed | −3.572 | 9.319 | .006 | −.278997 | .078101 | −.454758 | −.103236 |
| MMP2 | Equal variances assumed | 3.834 | 16 | .001 | .033111 | .008635 | .014805 | .051417 |
| | Equal variances not assumed | 3.834 | 15.566 | .002 | .033111 | .008635 | .014764 | .051459 |
| CEL | Equal variances assumed | −2.603 | 16 | .019 | −.508556 | .195401 | −.922788 | −.094323 |
| | Equal variances not assumed | −2.603 | 8.904 | .029 | −.508556 | .195401 | −.951308 | −.065803 |
| TF | Equal variances assumed | −.636 | 16 | .534 | −7.946667 | 12.495972 | −34.4369 | 18.543610 |
| | Equal variances not assumed | −.636 | 15.771 | .534 | −7.946667 | 12.495972 | −34.4682 | 18.574922 |

Example 2

Amniotic fluid (AF) is rich in proteins which may reflect the well-being of the fetus. It has been hypothesized herein that biomarkers for trisomy 21 exist in AF. A detailed comparison of AF from trisomy 21-affected pregnancies to AF from unaffected pregnancies was completed, with proteomic techniques using mass spectrometry (Examples 1; 5-6). Several candidate trisomy 21 biomarkers in AF were identified above, including mucin 13 (MUC13), which was found to be expressed at lower levels in trisomy 21 AF compared with unaffected fetuses.

MUC13 is a member of the transmembrane family of mucin proteins. The gene for MUC13 is found on human chromosome 3 and encodes a cell-surface glycoprotein shown to be highly expressed in the gastrointestinal tract and in some hematopoietic cells (27). MUC13 expression levels have been analyzed in association with gastric and ovarian cancers and in both cases, MUC13 expression was found to be increased in cancerous tissue compared to normal tissue (28, 29).

MUC13 protein levels in serum from pregnant and non-pregnant women are quantitated herein and the differential expression of MUC13 in serum from women carrying trisomy 21-affected compared to unaffected fetuses has been validated.

Materials and Methods
Patient Serum Samples

Serum samples (n=53) were obtained from the biochemistry lab at Mount Sinai Hospital. Samples from non-pregnant women were leftovers from routine testing (n=8). Samples from pregnant women, collected during the first (n=20) or second (n=25) trimester, were leftovers from testing performed as part of the hospital's maternal serum screening program. Samples were confirmed as being from women carrying normal (n=28) or trisomy 21 affected (n=17) fetuses by amniocentesis and fetal karyotype analysis by the cytogenetics lab at Mount Sinai.

Mucin 13 ELISA

A commercial MUC13 assay (USCN Life Science Inc., Wuhan, China) was used to measure MUC13 protein levels in patient serum. Briefly, 100 μL of undiluted serum or standards were added to wells of a microtiter plate, pre-coated with a monoclonal antibody specific for MUC13. Samples were incubated for 2 hours at 37° C. after which the samples were removed by washing and 100 μL of biotinylated polyclonal antibody specific for MUC13 were added to each well and incubated for 2 hours at 37° C. The plate was then washed 3 times in the manufacturer's prepared washing buffer after which 100 μL of avidin-linked horse radish peroxidase (HRP) were added and incubated for 30 minutes at 37° C. The plate was washed again, as described, and 90 μL of TMB substrate were added and incubated for 15 minutes at 37° C. Fifty μL of sulphuric acid solution were then added to stop the reaction following which the absorbance in each well was measured at 450 nm using a EnVision plate reader (Perkin Elmer, Woodbridge, ON). A standard curve was constructed and the concentration of MUC13 in each sample determined from the standard curve.

Statistics

All statistical analyses were performed using GraphPad Prism software version 4.02 (GraphPad Software, La Jolla, Calif., USA). Differences in MUC13 levels between sample groups were compared using the Mann-Whitney test and results were considered significant when $p<0.05$.

Results

MUC13 Levels in Serum from Pregnant and Non-Pregnant Women

Figure 4:
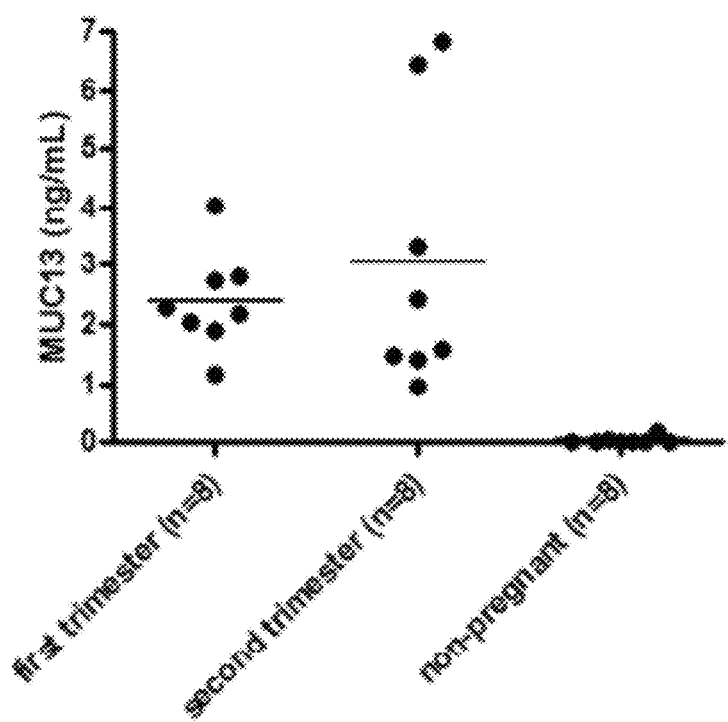
FIG. 4. MUC13 protein levels were measured in serum from non-pregnant (n=8) and pregnant women during the first (n=8) and second (n=8) trimesters of pregnancy by ELISA. MUC13 levels were almost undetectable in serum from non-pregnant women but were quantifiable in serum from pregnant women. Mean MUC13 levels are indicated by the horizontal line.

MUC13 levels were measured in serum from non-pregnant women (n=8) and pregnant women (trisomy 21 unaffected) in the first (n=8) and second trimester (n=8) of pregnancy by ELISA. MUC13 levels were higher in serum from pregnant women compared to non-pregnant women (FIG. 4). MUC13 levels could only be quantified in two of the serum samples from non-pregnant women because in the remaining six samples levels were below the detection limit of the assay. MUC13 levels also appeared to be higher in the second trimester of pregnancy compared to the first trimester (FIG. 4).

Figure 5:
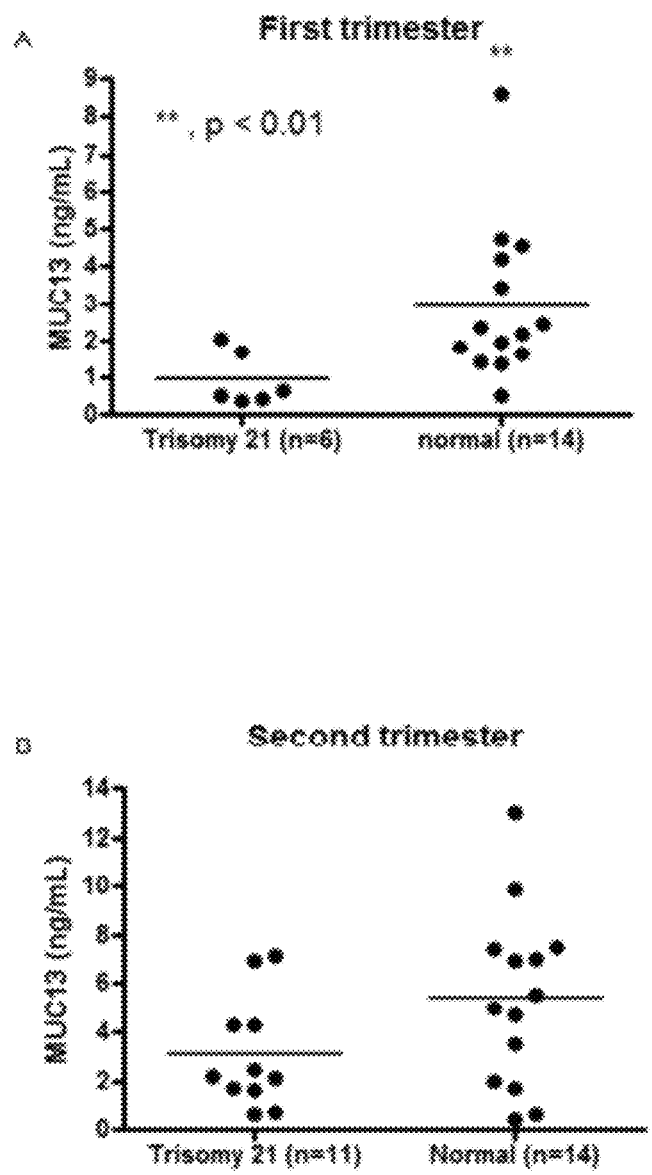
FIG. 5. A) MUC13 protein levels were measured in serum from pregnant women carrying trisomy 21-affected (n=6) and non-affected (n=14) fetuses during the first trimester of pregnancy, by ELISA. Serum MUC13 levels were significantly lower (p<0.01) in serum from women carrying trisomy 21-affected fetuses compared to levels in serum from women carrying unaffected fetuses. B) MUC13 protein levels were measured in serum from pregnant women carrying trisomy 21-affected (n=11) and non-affected (n=14) during the second trimester of pregnancy, by ELISA. MUC13 levels were lower in serum from women carrying trisomy 21-affected fetuses compared to non-affected. Mean MUC13 levels are indicated by the horizontal line. The differences did not reach statistical significance.

MUC13 Levels in Serum from Women Carrying Trisomy 21-Affected Versus Non-Affected Fetuses MUC13 levels were measured in serum samples from women carrying trisomy 21-affected (n=6, first trimester; n=11, second trimester) or unaffected fetuses (n=14, first trimester; n=14, second trimester) by ELISA. MUC13 levels were significantly lower in first trimester serum from women carrying trisomy 21-affected fetuses compared to unaffected fetuses ($p<0.01$; FIG. 5A). MUC13 levels were also lower in second trimester serum from women carrying trisomy 21-affected fetuses compared to unaffected fetuses, however these results did not reach statistical significance (FIG. 5B).

Discussion

Here, MUC13, a transmembrane mucin glycoprotein, is reported as a candidate maternal serum biomarker for trisomy 21. MUC13 levels appear to be pregnancy-specific as levels were almost undetectable in serum from non-pregnant women but were quantifiable in serum from pregnant women by ELISA. In addition, maternal serum MUC13 levels appear to increase with increased gestation. Significantly lower levels of MUC13 present in maternal serum from women carrying trisomy 21-affected fetuses compared to serum from women carrying unaffected fetuses have been demonstrated. Although these results are representative of a relatively small sample size, they are encouraging given that MUC13 appears to be pregnancy-specific and potentially useful as a first trimester marker.

Several other mucin proteins have shown utility as biomarkers for various malignancies and are currently in use clinically. These include the breast cancer markers CA 15-3 and CA 549, the ovarian cancer marker CA-125, the pancreatic cancer CA19.9 and mucin 16 for cervical cancer (29-33).

The function of MUC13 is largely unknown, however these findings suggest that MUC13 may be important in human placentation and fetal development. It can be speculated that this protein may be specifically involved in the development of the gastrointestinal tract and in fetal hematopoiesis. Gastrointestinal defects and an increased risk of leukemia are two features of Down syndrome and it could be that reduced MUC13 expression in Trisomy 21 plays a role in these manifestations.

Current screening modalities for trisomy 21 lack the desired levels of specificity and sensitivity required for patients to make decisions about their pregnancies early on in gestation. In addition, current methods generate high numbers of false positive results which require amniocentesis for confirmation. There is a need for new or additional trisomy 21 biomarkers, ideally suitable for maternal serum screening in the first and second trimester of pregnancy. Here, MUC13 is described as a potential new candidate first and second trimester, maternal serum marker for trisomy 21. These findings are encouraging and ongoing studies, including larger numbers of patients will confirm the utility of MUC13 as a marker for trisomy 21. Its combination with the currently used biomarkers will show if it can further improve specificity and reduce the number of performed amniocenteses.

Example 3

Measurement of Two Candidates in Individual AF and Serum

The concentration of APP and Tenascin-C was measured using sandwich ELISA with a Human APP ELISA kit (US Biological, MA) and a Tenascin-C Large (FNIII-B) Assay kit (Immuno-Biological Laboratories), respectively. Individual AF samples, which were used to create the pools for MS/MS analysis (n=10 per group; CN or DS), as well as an additional eight, randomly selected CN-AF samples, were measured, along with unmatched serum samples (true positives and true negatives by cytogenetic analysis). A 100-fold dilution of the samples was prepared for both AF and serum samples to measure APP, and a 400-fold dilution was prepared for both AF and serum for TNC-C assay. Both ELISAs were performed according to the instructions provided with the kit, and results were analyzed using GraphPAD Prism (GraphPAD Software, San Diego, Calif.). Statistical analysis was performed using onefactorial analysis of variance (ANOVA) and independent samples t test. Values of p<0.05 were considered significant Examination of Two Candidates by ELISA.

Figure 6:
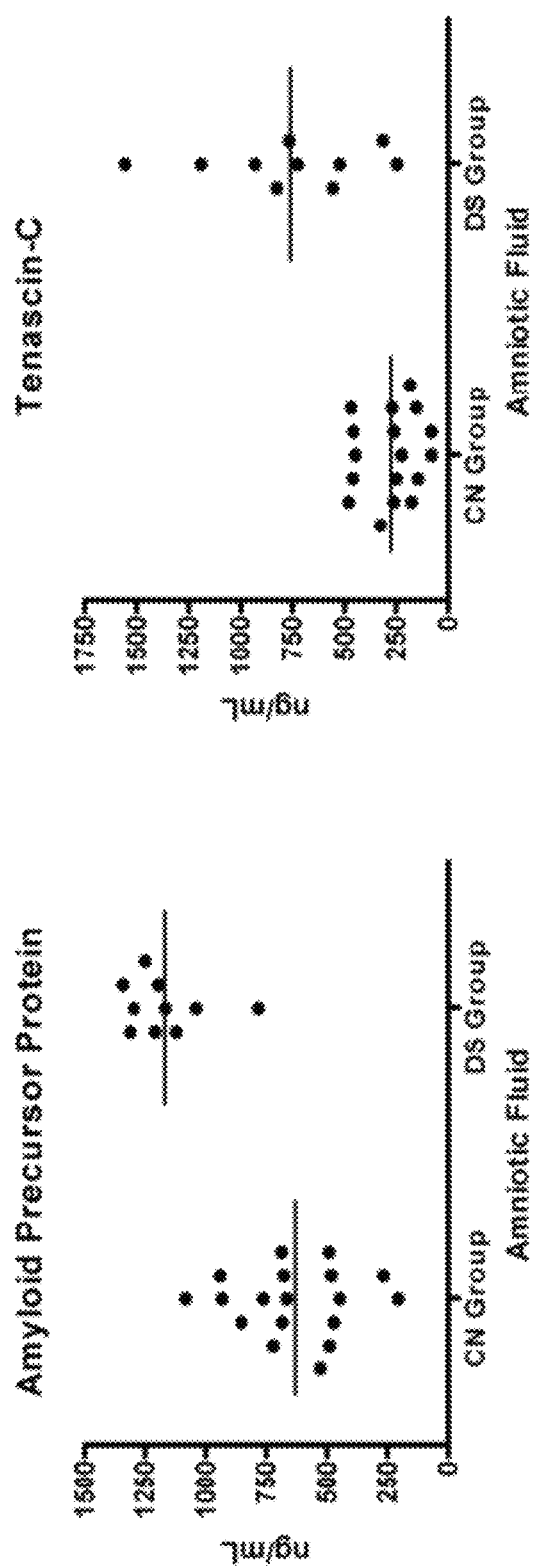
FIG. 6. Verification of two candidates in amniotic fluid by ELISA. (A) APP; (B) TNC-C. CN=chromosomally normal and DS=Down syndrome pregnancies.

From the list of 60 candidates previously identified, two were selected for further verification using a more sensitive and specific quantification method (ELISA): amyloid precursor protein (APP) and tenascin-C (TNC-C). APP was one of the candidates that were included in the final list of candidates, not because of its substantial increase in DS-AF, but due to location of the gene on chromosome 21. To verify the spectral counting result, an increase of 63% in number of spectra in DS-AF, APP levels were measured in DS-AF samples (n=10) and CN-AF samples (n=18; 10 matched for gestational age and 8 randomly selected) by ELISA. The mean concentration of APP was 630 ng/mL in the CN group, and 1170 ng/mL in the DS group (FIG. 6a). The mean concentration was significantly higher in the DS group than the CN group (p<0.001). The same ELISA kit was used to measure APP levels in maternal serum samples from DS (n=8) and CN (n=36) pregnancies, but there was no statistically significant difference between the two groups.

TNC-C was selected for two reasons: it exhibited a relatively high DS to CN spectral count ratio of 2.9, and previous studies suggested that TNC-C may have an important role in development of multiple organs (34-37), leading us to hypothesize that TNC-C may have a potential impact on the phenotype of DS. TNC-C levels were measured in the DS-AF samples (n=10) and CN-AF samples (n=17; 10 matched for gestational age and 7 randomly selected) by ELISA. The mean concentration of TNC-C was 274 ng/mL in the CN group, and 759 ng/mL in the DS group (FIG. 6b). The mean concentration of TNC-C was significantly higher in the DS group than the CN group (p=0.004). TNC-C levels were also measured in maternal serum samples from DS (n=11) and CN (n=24) pregnancies, using the same ELISA kit, but no statistically significant difference was found between the two groups.

Example 4

Quantification and Verification of Three Biomarkers of DS Using the SRM Technology A mass spectrometry-based SRM assay was developed to quantify the biomarkers CEL, CPA1 and MUC13 in AF samples from pregnant women with gestational age between 15 and 17 weeks and affected or non-affected fetuses.

Material and Methods

Materials

RapiGest SF Surfactant was purchased from Waters (Milford, Mass., USA). Dithiothreitol, iodoacetamide and trifluoroacetic acid were from Sigma-Aldrich (St. Louis, Mo., USA). Sequencing grade modified trypsin was from Promega (Madison, Wis., USA). Ammonium bicarbonate and acetonitrile (grade HPLC) were from Fisher Scientific (New Jersey, USA). Heavy peptides (Tagged SpikeTides TQL) were from JPT Peptide Technologies (Berlin, Germany). OMIX C18 tips were from Varian (Lake Forest, Calif., USA).

Amniotic Fluid Samples

AF samples (n=54) were obtained from pregnant women, with gestational ages ranging from 15+0 to 17+5 weeks, who underwent amniocentesis and fetal karyotype analysis by the cytogenetics lab at Mount Sinai Hospital (Toronto). Samples were confirmed as being from women carrying chromosomally normal (CN) (n=37) or DS affected (n=17) fetuses. These samples were stored at −80° C. until analyzed. The results of alfa-fetoprotein (AFP), in concentration (μg/ml) and multiple of expected median (MoM), measured in these samples for the screening of neural tube defects, with an AutoDelfia analyzer (Perkin Elmer, Turku, Finland), were collected and used as an external control. Our protocol has been approved by the Institutional Review Board of Mount Sinai Hospital, Toronto, Canada.

Peptide Selection for SRM Assays

Unique peptides (proteotypic) for each protein were manually chosen in Scaffold (Proteome Software) using the identification data acquired from an LTQ Orbitrap XL instrument (Thermo Scientific Inc.). Peptides that had clear and intense y-ion fragments, a length of 8 to 20 amino acids and without methionine residues were selected. Peptide uniqueness was confirmed by searching against the Basic Local Alignment Search Tool (BLAST) (38). When more than one candidate peptide for a single protein was selected, the peptide with more intense transitions, without interferences and with less overlapping in retention time with other peptides was preferred.

Sample Preparation

Before analysis, AF samples were thawed at room temperature and centrifuged at 13,500 rpm for 10 min. to eliminate cells and other cellular debris. Then, samples were diluted 6-fold with 50 mM ammonium bicarbonate and 9 μL of diluted samples were processed. The proteins were denatured with 0.1% RapiGest for 15 min. at 80° C. Reduction and alkylation were performed using 15 mM dithiothreitol for 15 min. at 70° C. and 25 mM iodoacetamide for 40 min. at room temperature and in the dark, respectively. Then, a mixture with 65 fmoles of each isotopically labeled peptide was added and the proteins/heavy peptides were digested with trypsin for 21 hours at 37° C. (weight dilution of 1/30 enzyme/substrate). The total protein concentration in each sample was determined using the Coomassie Plus (Bradford) protein assay (Thermo Fisher Scientific). After trypsinization, RapiGest was cleaved with 1% trifluoroacetic acid, and samples were centrifuged at 1500 rpm for 30 min. Peptides were purified and extracted using 10 μL OMIX C18 tips, and then eluted using 5 μL of 65% acetonitrile solution (0.1% formic acid). The final sample was diluted to 130 μL with water (0.1% formic acid) to yield three replicates of 40 μL. All these steps were performed in a 96 well plate.

LC-SRM-MS Conditions

AF samples were loaded onto a 2 cm trap column (C18, 5 μm) with an inner diameter of 150 μm and the peptides were eluted onto a resolving 5 cm analytical column (C18, 3 μm) with an inner diameter of 75 μm and 15 μm tip (New Objective). The LC setup, EASY-nLC (Proxeon A/S), was coupled online to a triple-quadrupole mass spectrometer (TSQ Vantage, Thermo Fisher Scientific Inc.) using a nanoelectrospray ionization source (nano-ESI, Proxeon A/S). A three-step gradient with an injection volume of 40 μL was used. Buffer A contained 0.1% formic acid in water, and buffer B contained 0.1% formic acid in acetonitrile. A 54/59 min. method with 30/35 min. gradient was used for initial identification of peptides and light/heavy peptide quantification, respectively. Peptides were analyzed by SRM methods with the following parameters: positive-ion mode, predicted collision energy values, 1.5 s cycle time, 0.2 Da of full width half maximum in Q1 and 0.7 Da in Q3, 1.5 mTorr Q2 pressure, tuned tube lens values and 1 V skimmer offset. Three transitions for each light/heavy peptides were monitored (Table 4A). In silico digestion and fragmentation, prediction of collision energy and analysis of results were performed using Pinpoint 1.0 software (Thermo Scientific Inc.). Skyline (MacCoss Lab) (39) software was used to predict the retention time of peptides in the initial identification.

Statistical Analysis

Statistical analyses were performed with SPSS® 15.0 software package (SPSS Inc., Chicago, Ill., USA). A p-value<0.05 was considered statistically significant. Normal distribution was evaluated using Shapiro-Wilk test and by inspection of Q-Q plots. Student's t or Mann-Whitney U tests were performed for comparison between independent samples. Receiver-operating characteristic (ROC) curves were plotted and areas under curve (AUC), with a 95% confidence interval (CI), were calculated.

Results

Analysis of Proteins and Selection of Proteotypic Peptides

A total of 3 candidate proteins were analyzed: bile salt-activated lipase (CEL), carboxypeptidase A1 (CPA1) and mucin 13 (MUC13). Moreover, two more proteins (human chorionic gonadotropin beta (β-hCG) and transferrin (TF)) used as internal controls were included in the analysis. The β-hCG was selected as positive control, since it is a known biomarker of DS, and TF was selected as negative control. Between 1 and 3 proteotypic peptides for each protein were analyzed to finally select the peptide with the best analytical features.

Confirmation of Peptide Identification

Figure 9A:
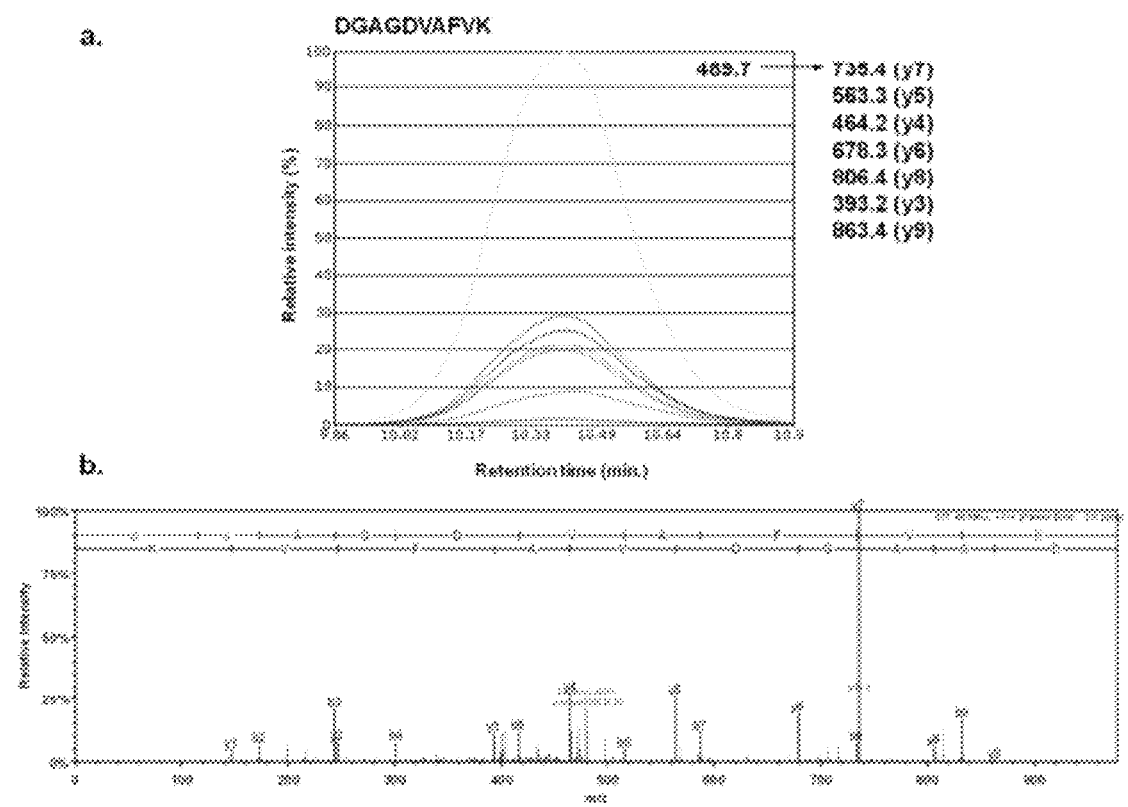
FIG. 9A. Co-elution of transitions for DGAGDVAFVK peptide in the TSQ Vantage (a) and pattern of fragmentation in the LTQ Orbitrap XL (b).

The identity of peptides was confirmed by four different ways. First, by prediction of retention times using SRRCalc 3.0 from Skyline software, formula to predict the retention time according to the hydrophobicity of peptide (Table 4B). Second, by analysis of correlation between retention times in the discovery stage with an LTQ Orbitrap XL (60 min. gradient) and verification stage with a TSQ Vantage (30 min. gradient). Third, observing the co-elution of at least 6 transitions for each peptide analyzed. Fourth, comparing the fragmentation pattern (similar intensity of transitions) in the LTQ Orbitrap XL and TSQ Vantage (FIG. 9A).

Analysis of Individual Amniotic Fluid Samples

Figure 9B:
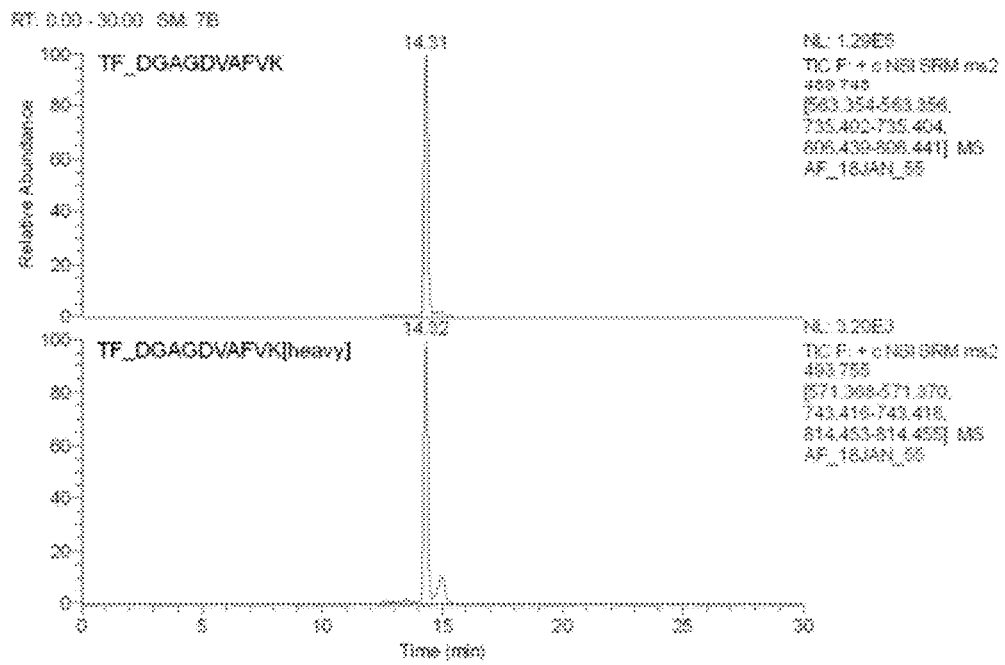
FIG. 9B. SRM analysis of 5 endogenous tryptic peptides (upper panel) and 5 heavy-isotope labeled synthetic peptides (lower panel) in an amniotic fluid sample. Each LC-MS injection had 20 fmoles on column of each heavy peptide standard. Three transitions per each peptide were monitored.
Figure 9B:
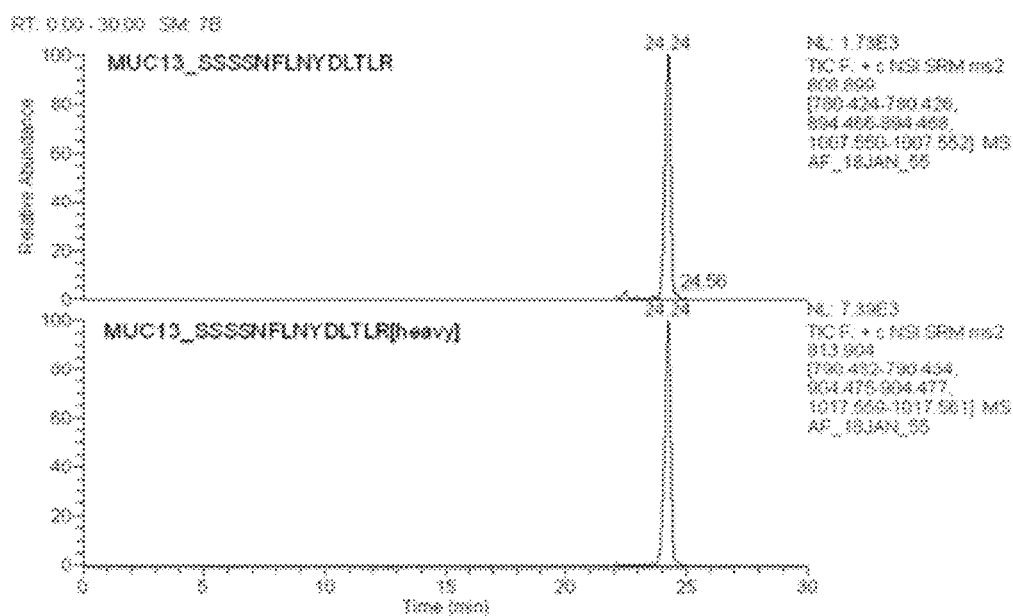
Figure 9B:
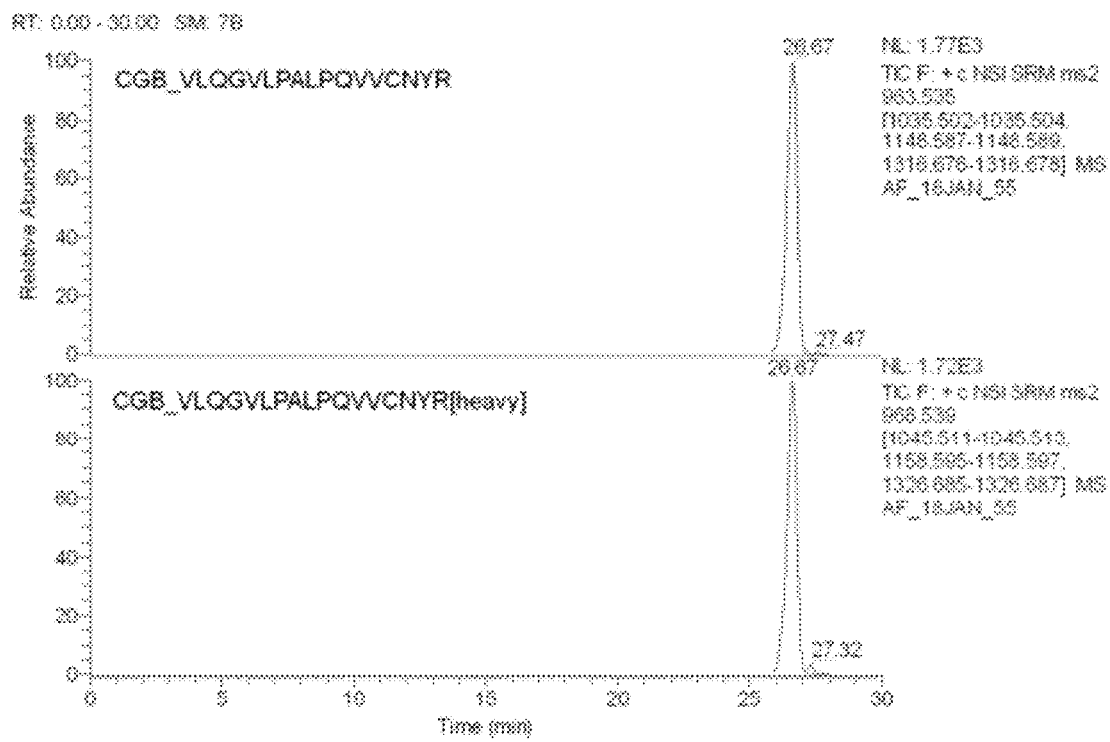
Figure 9B:
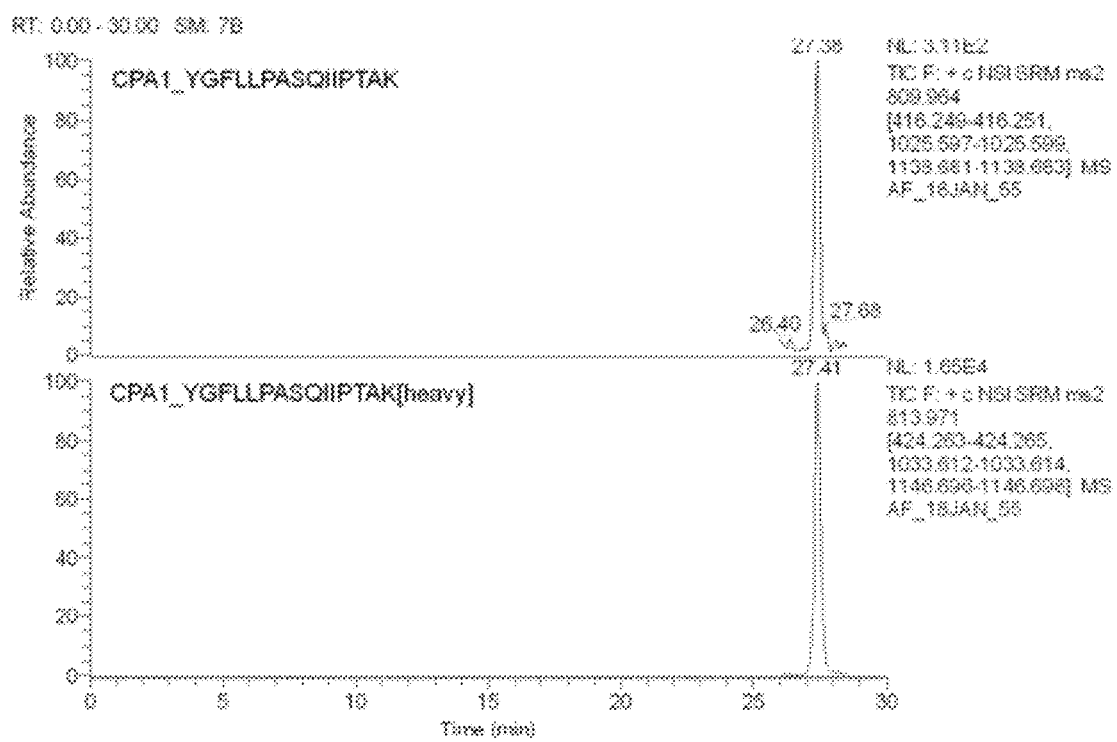
Figure 9B:
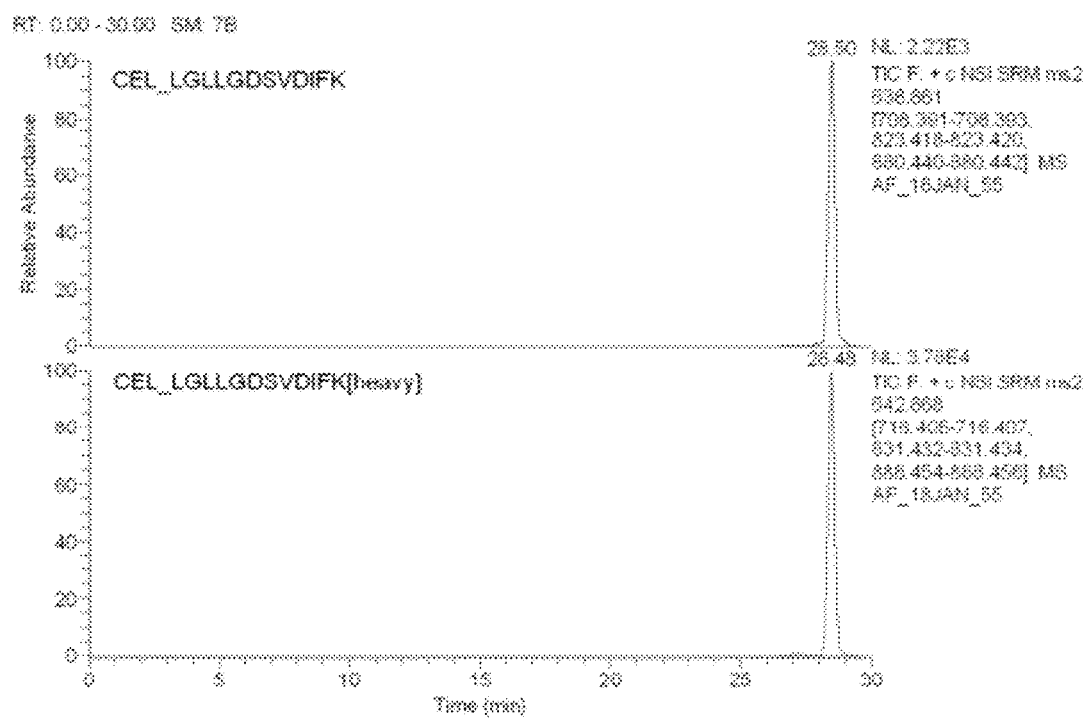

AF samples (with spiked heavy peptide standards) were analyzed sequentially and in a stochastic order. The peak area for each endogenous peptide was integrated and the concentration was calculated by extrapolation with the area of internal standard (FIG. 9B). The protein concentration was calculated assuming a ratio peptide/protein of 1:1 and using the molecular weight corresponding to the complete sequence of each protein. Three injections (SRM runs) per sample were performed to estimate the reproducibility of analysis. The average coefficient of variation (CV) for the five peptides was from 4 to 12%, with an overall CV lower than 7%. Additionally, the concentration of AFP in these AF samples was used as an external control for subsequent analyses.

Figure 7A:
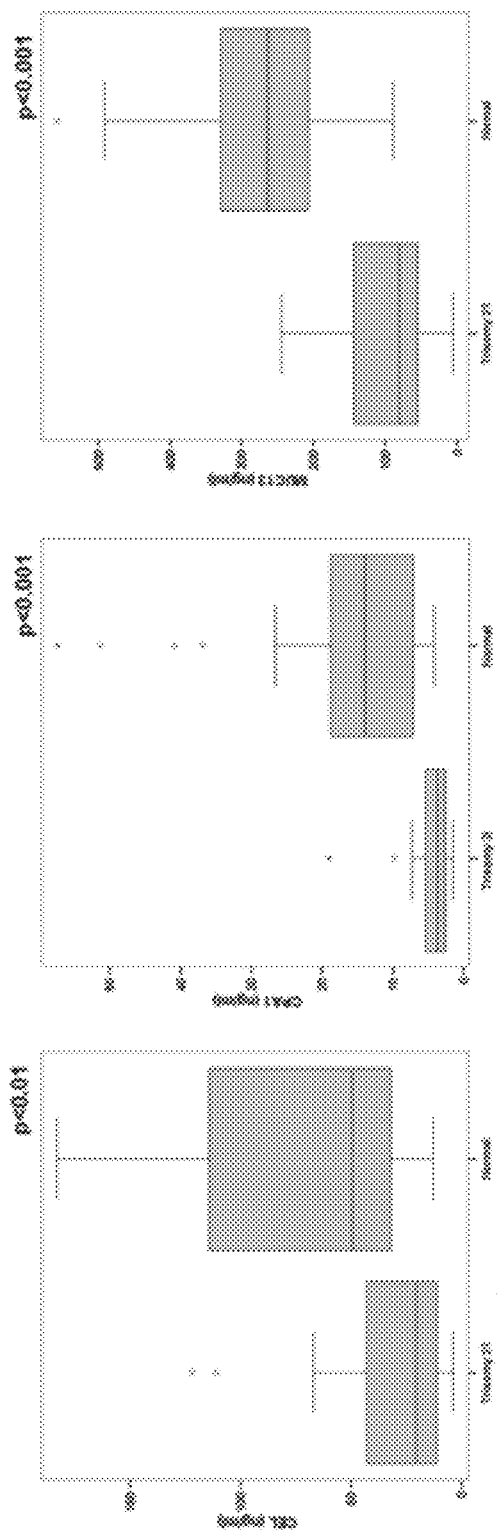
FIG. 7. Box and Whisker diagrams for CEL, CPA1 and MUC13 proteins (A), and TF, CGB and AFP proteins (B), in trisomy 21 (n=17) and chromosomally normal amniotic fluid samples (n=37).
Figure 7B:
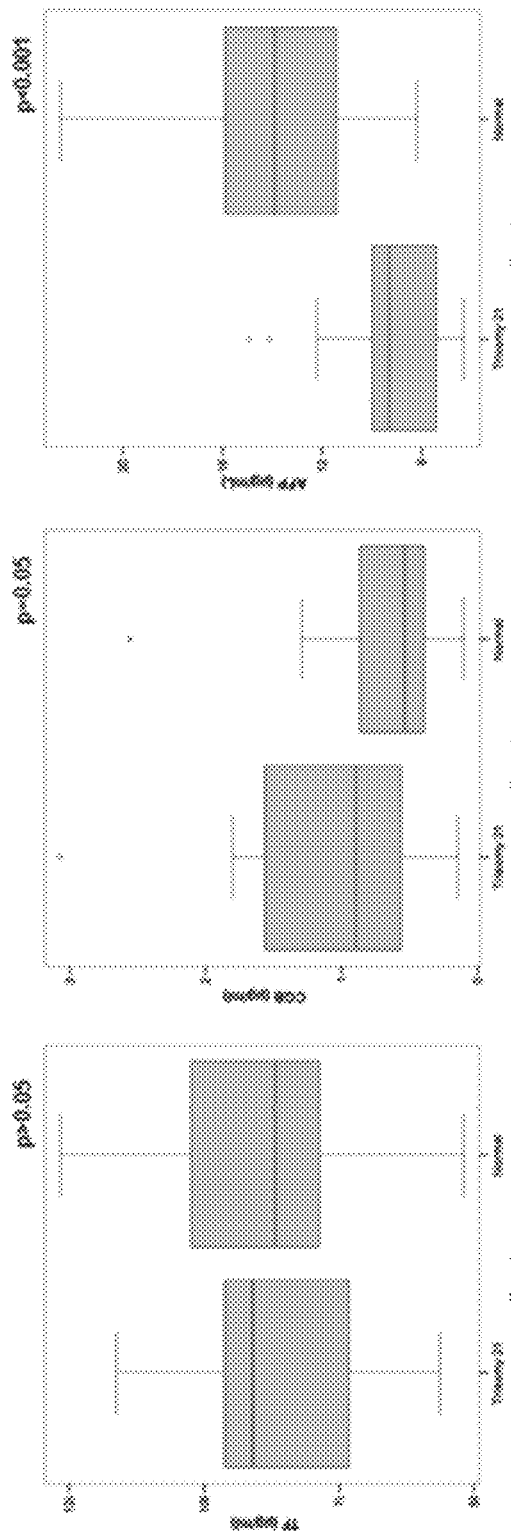

The median protein concentrations for DS and CN samples were: 20 and 49 ng/ml (p<0.01) for CEL; 3.7 and 14 ng/ml (p<0.001) for CPA1; 80 and 263 ng/ml (p<0.001) for MUC13 (FIG. 7A); 91 and 87 μg/ml (p>0.05) for TF; 0.89 and 0.54 μg/ml (p=0.05) for β-hCG; 9.3 and 13.9 μg/ml (p<0.001) for AFP (FIG. 7B). The mean gestational age was 114 days in both groups of samples.

Figure 8A:
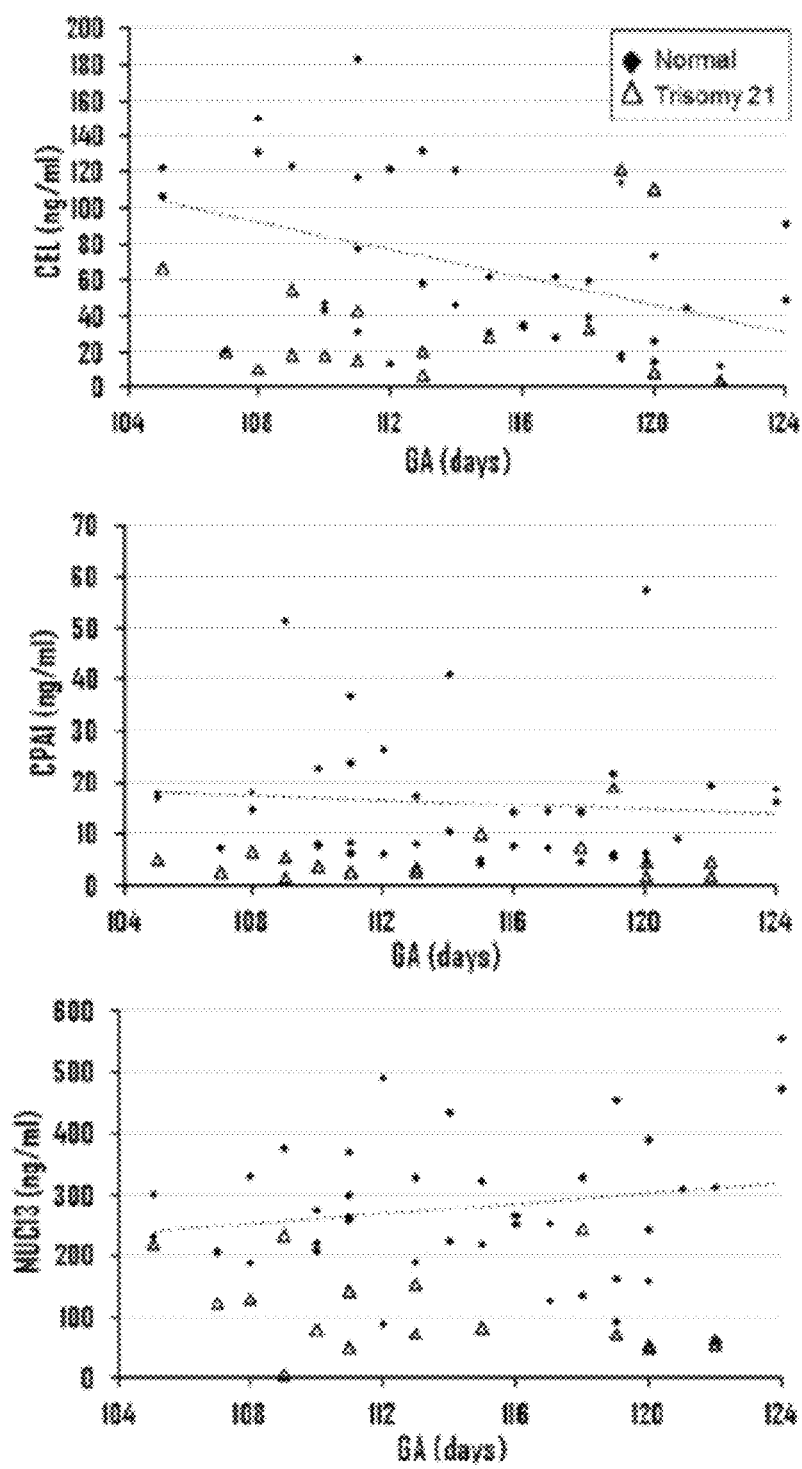
FIG. 8. Concentrations of CEL, CPA1 and MUC13 (A), and TF, CGB and AFP (B), according to the gestational age (from 105 to 124 days). The filled diamonds and open triangles represent the normal and trisomy 21 samples, respectively. The dashed line represents the estimation of median values in chromosomally normal pregnancies.
Figure 8B:
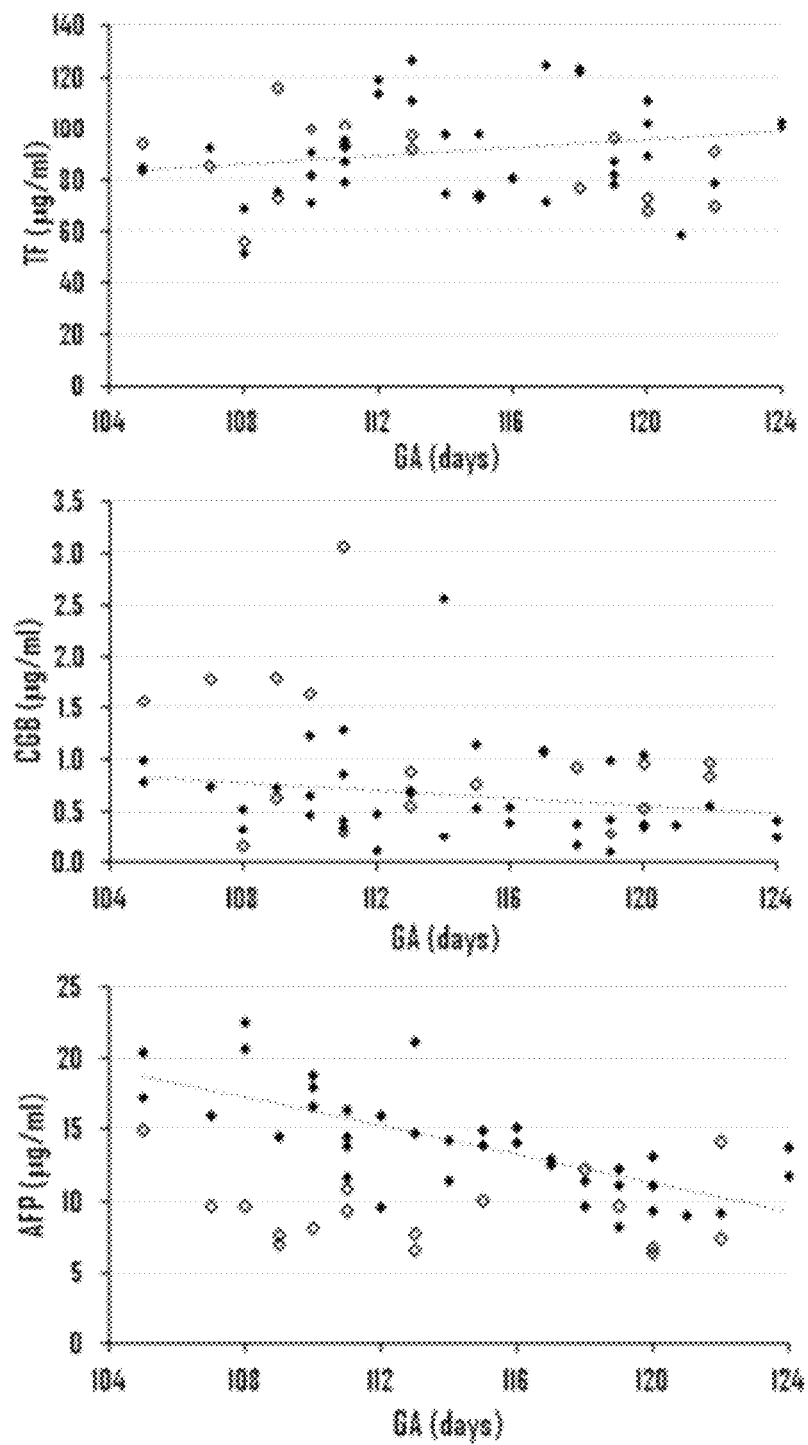

Moreover, the concentrations were plotted according to gestational age (FIGS. 8A and B) and the results from CN samples were used to estimate the median protein concentration, by calculation of linear regression. Then, the concentrations were transformed to MoM and the ratio DS/CN of median MoM was calculated (Table 4C), resulting: CEL (0.23), CPA1 (0.26), MUC13 (0.30), TF (1.00), β-hCG (1.81) and AFP (0.59). The MoMs of AFP obtained with this approximation were compared with the MoMs obtained using the regression line of medians from the screening program of neural tube defects, resulting in a difference of MoMs from −6.3% to +10.6%.

TABLE 4A

SRM parameters used for each proteotypic peptide.

| Protein | Proteotypic peptide | Retention time, min. | Precursor m/z | Collision energy, eV | Fragments m/z |
|---------|---------------------|----------------------|---------------|----------------------|---------------|
| TF | DGAGDVAFVK (SEQ ID NO: 14) | 14.3 | 489.748 | 19.9 | 563.355<br>735.403<br>806.440 |
| TF | DGAGDVAFVK[heavy] SEQ ID NO: 14) | 14.3 | 493.755 | 20.1 | 571.369<br>743.417<br>814.454 |
| MUC13 | SSSSNFLNYDLTLR SEQ ID NO: 2) | 24.2 | 808.899 | 30.8 | 780.425<br>894.467<br>1007.551 |
| MUC13 | SSSSNFLNYDLTLR[heavy] SEQ ID NO: 2) | 24.2 | 813.904 | 30.9 | 790.433<br>904.476<br>1017.56 |
| CGB | VLQGVLPALPQVVCNYR SEQ ID NO: 16) | 26.7 | 963.535 | 36.0 | 1035.503<br>1148.588<br>1316.677 |
| CGB | VLQGVLPALPQVVCNYR[heavy] SEQ ID NO: 16) | 26.7 | 968.539 | 36.2 | 1045.512<br>1158.596<br>1326.686 |
| CPA1 | YGFLLPASQIIPTAK SEQ ID NO: 17) | 27.4 | 809.964 | 30.8 | 416.250<br>1025.599<br>1138.682 |
| CPA1 | YGFLLPASQIIPTAK[heavy] SEQ ID NO: 17) | 27.4 | 813.971 | 30.9 | 424.264<br>1033.613<br>1146.697 |
| CEL | LGLLGDSVDIFK SEQ ID NO: 1) | 28.5 | 638.861 | 25.0 | 708.392<br>823.419<br>880.441 |
| CEL | LGLLGDSVDIFK[heavy] SEQ ID NO: 1) | 28.5 | 642.868 | 25.1 | 716.406<br>831.433<br>888.455 |

TABLE 4B

Predicted retention times for proteotypic peptides using Skyline software.

| Protein | Peptide | Retention time (min.) | Predicted time* (min.) |
|---------|---------|------------------------|-------------------------|
| TF | DGAGDVAFVK (SEQ ID NO: 14) | 10.4 | 10.2-13.0 |
| MUC13 | SSSSNFLNYDLTLR (SEQ ID NO: 2) | 17.4 | 16.2-19.0 |
| CGB | VLQGVLPALPQVVCNYR (SEQ ID NO: 16) | 19.5 | 18.0-20.8 |
| CPA1 | YGFLLPASQIIPTAK (SEQ ID NO: 17) | 20.3 | 17.6-20.4 |
| CEL | LGLLGDSVDIFK (SEQ ID NO: 1) | 20.9 | 18.1-20.9 |

*calculated with formula SRRCalc 3.0 (100 Å), 95% confidence interval

A 0.2 mg/ml bovine serum albumin (BSA) solution was prepared and analyzed in the same conditions as one AF pool of samples and the retention times for 18 BSA peptides were obtained and used in the SRRCalc 3.0 to calculate the linear regression (hydrophobicity versus retention time).

TABLE 4C

Median of multiple of expected median (MoM) in cases of trisomy 21 and normal karyotype, for each protein.

| Protein | Median (MoM) | | Ratio |
|---|---|---|---|
| | Trisomy 21 | Normal karyotype | Trisomy 21/Normal |
| CEL | 0.22 | 0.94 | 0.23 |
| CPA1 | 0.22 | 0.84 | 0.26 |
| MUC13 | 0.30 | 0.98 | 0.30 |
| TF | 1.00 | 1.00 | 1.00 |
| β-hCG | 1.56 | 0.86 | 1.81 |
| AFP | 0.59 | 1.00 | 0.59 |

Figure 10:
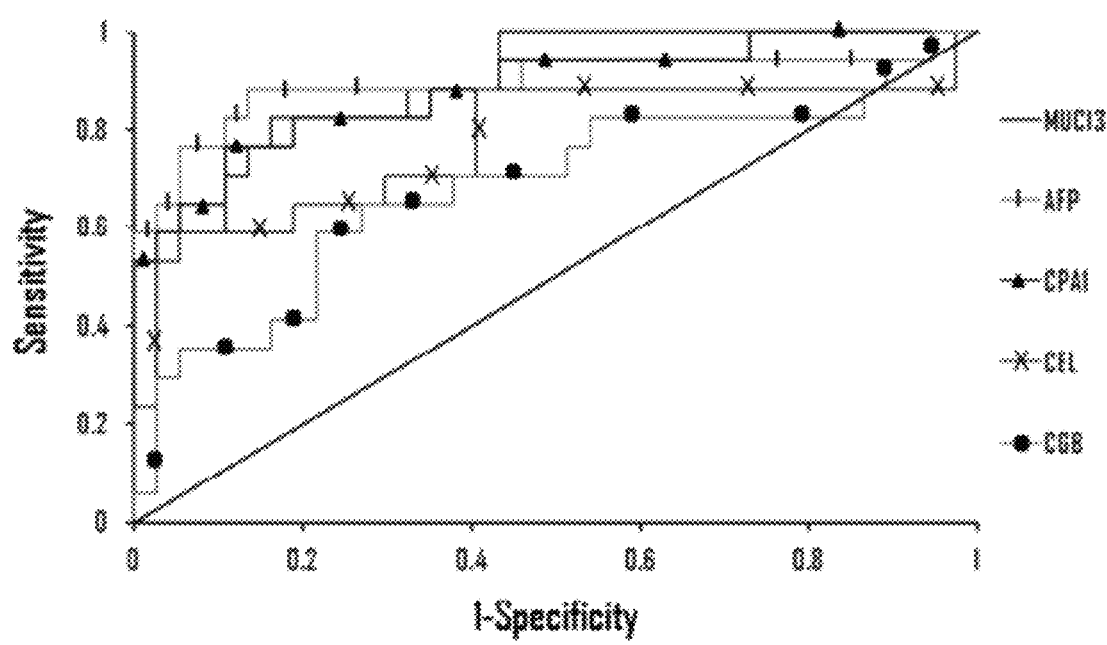
FIG. 10. Receiver-operating characteristic (ROC) curves for candidate proteins (CEL, CPA1 and MUC13) and positive controls (CGB and AFP).

The MoMs obtained for all patients (n=54) were used to calculate the ROC curve and the corresponding AUC for candidate proteins (MUC13, CPA1 and CEL) and positive controls (β-hCG and AFP) (Table 5 and FIG. 10). MUC13 showed the greatest AUC (0.90; 95% CI: 0.81-0.98), followed by AFP (0.89; 95% CI: 0.78-1.01) and CPA1 (0.88; 95% CI: 0.78-0.99).

TABLE 5

Area under the curve (AUC) and confidence interval at 95% (95% CI), for each candidate protein (CEL, CPA1 and MUC13) and positive controls (β-hCGand AFP).

| Protein | AUC | 95% CI |
|---|---|---|
| MUC13 | 0.90 | 0.81-0.98 |
| AFP | 0.89 | 0.78-1.01 |
| CPA1 | 0.88 | 0.78-0.99 |
| CEL | 0.77 | 0.62-0.93 |
| β-hCG | 0.68 | 0.52-0.85 |

Moreover, the detection rate for these proteins was calculated by fixing the FPR at 0, 2.7 and 5.4%, respectively (Table 6). At 5.4% FPR, AFP showed the greatest detection rate (76%) followed by CPA1 (65%) and MUC13 and CEL (59%).

TABLE 6

Detection rate (%) obtained for each candidate protein and positive controls at 0, 2.7 and 5.4% false-positive rate (FPR), respectively.

| FPR (%) | Detection rate (%) | | | | |
|---|---|---|---|---|---|
| | CEL | CPA1 | MUC13 | β-hCG | AFP |
| 0.0 | 24 | 53 | 59 | 6 | 59 |
| 2.7 | 53 | 59 | 59 | 29 | 65 |
| 5.4 | 59 | 65 | 59 | 35 | 76 |

Finally, the comparison of MoMs obtained in the cases of DS (Table 7) shows that candidate proteins may generate different and complementary information to that provided by known biomarkers, as in cases 7, 11 and 13 where the results of β-hCG and AFP weakly (or not) increase the risk of DS and the results of some of the candidate proteins are very abnormal.

TABLE 7

Multiple of expected median (MoM) for candidate proteins and positive controls (β-hCGand AFP) in all cases of trisomy 21 (n = 17).

| | | MoM | | | | |
|---|---|---|---|---|---|---|
| No | GA (days) | CEL | CPA1 | MUC13 | β-hCG | AFP |
| 1 | 105 | 0.68 | 0.33* | 0.93 | 2.17** | 0.79 |
| 2 | 107 | 0.23* | 0.18* | 0.50* | 2.59** | 0.54* |
| 3 | 108 | 0.13* | 0.45* | 0.53* | 0.22 | 0.56* |
| 4 | 109 | 0.66* | 0.38* | 0.93 | 0.97 | 0.42* |
| 5 | 109 | 0.22* | 0.11* | 0.02* | 2.74** | 0.45* |
| 6 | 110 | 0.23* | 0.26* | 0.31* | 2.57** | 0.50* |
| 7 | 111 | 0.56* | 0.18* | 0.55* | 0.47 | 0.68 |
| 8 | 111 | 0.21* | 0.19* | 0.19* | 4.90** | 0.59* |
| 9 | 113 | 0.30* | 0.20* | 0.27* | 1.50** | 0.45* |
| 10 | 113 | 0.10* | 0.25* | 0.57* | 0.94 | 0.52* |
| 11 | 115 | 0.47* | 0.75 | 0.30* | 1.37 | 0.73 |
| 12 | 118 | 0.66* | 0.58* | 0.84 | 1.80** | 1.00 |
| 13 | 119 | 2.58 | 1.53 | 0.24* | 0.55 | 0.82 |
| 14 | 120 | 2.55 | 0.37* | 0.18* | 1.11 | 0.56* |
| 15 | 120 | 0.19* | 0.14* | 0.16* | 1.99** | 0.60* |
| 16 | 122 | 0.11* | 0.38* | 0.21* | 2.14** | 1.38 |
| 17 | 122 | 0.10* | 0.14* | 0.18* | 1.84** | 0.72 |

GA = gestational age
The MoM obtained for each case of trisomy 21 was corrected by the median MoM of all chromosomally normal cases.
Cases with values ≥1.5 or ≤0.67 are marked as ** and *, respectively.

Discussion

In this Example, the quantification and verification of three potential biomarkers of DS using the SRM technology is presented.

The AF samples analyzed were from pregnant women with gestational ages ranging from 15+0 to 17+5 weeks. The purpose was to study the candidate proteins in a narrow gestational interval, to reduce the variability of protein concentration due to the evolution of pregnancy and, at the same time, maximize the likelihood to find a useful biomarker in first and/or second trimesters of pregnancy since these gestational weeks are the closest to first trimester, in which the amniocentesis can be performed.

The results obtained in the fifty-four samples assayed indicate that the three proteins studied are potential candidates for the detection of DS showing a significant down-regulation. The inclusion in the analysis of positive (β-hCG and AFP) and negative (TF) controls allowed for increased confidence in the obtained results. Thus, the comparison of concentrations (in CN and DS samples) for TF (negative control) did not show significant differences and for β-hCG (positive control) were within the limit of significance (p=0.05). The subsequent estimation of medians and calculation of MoMs seems to be reasonable since for AFP, the differences found between the estimated MoMs and the MoMs used in the screening program of neural tube defects were ±10%. The median MoM obtained for DS cases, after correction with the value for CN cases, was 1.00 MoM (for TF), 1.81 MoM (for β-hCG) and 0.59 MoM (for AFP). It is important to point out that due to the technology used (SRM) the results for β-hCG correspond to total hCG. Similar results were described by Spencer et al.(40) for β-hCG (1.84 MoM) and AFP (0.56 MoM), using immunoassays and AF samples from pregnant women carrying DS (n=91) or CN (n=240) fetuses, at 15-21 gestational weeks. Therefore, the negative control did not show any difference between groups and the positive controls showed very similar differences to those described previously.

With respect to the candidates, MUC13 is a transmembrane glycoprotein normally localized to the apical surface of epithelial cells in the gastrointestinal system, playing a role in protection and lubrication of the mucosal surface (41). However, the regulation of MUC13 expression has not been studied yet. CEL and CPA1 are two proteins highly expressed in pancreas. CEL is synthesized primarily in the acinar cells of the pancreas and it is secreted into the lumen of the intestine. This protein catalyzes the hydrolysis of cholesteryl esters to non-esterified cholesterol and fatty acids (42) but its role in hepatic and plasma cholesterol metabolism remain unclear. Interestingly, DS appears to be a protective factor regarding the development of atherosclerosis and higher levels of cholesterol in blood samples of fetuses with DS have been reported (25). Finally, CPA1 is a monomeric pancreatic exopeptidase involved in zymogen inhibition but with unknown biological function.

Conclusion

Statistically significant differences were found in the three proteins analyzed, reflecting a different regulation in DS. These proteins may be useful biomarkers in the screening of this pathology in the first and/or second trimesters of gestation.

Example 5

The following combinations of markers were tested. The AUC (as described in Example 1) for the following biomarkers alone and in various combinations are provided in Tables 8 and 9, respectively.

TABLE 8

Area under the curve (AUC) for candidate proteins (CEL, CPA1 and MUC13) and positive controls (β-hCG and AFP).

| Predictor | AUC |
| --- | --- |
| MUC13 | 0.90 |
| AFP | 0.89 |
| CPA1 | 0.88 |
| CEL | 0.77 |
| β-hCG | 0.68 |

TABLE 9

Area under the curve (AUC) for various combinations of candidate proteins and positive controls.

| Predictor 1 | Predictor 2 | AUC |
| --- | --- | --- |
| MUC13 | AFP | 0.94 |
| MUC13 | CPA1 | 0.92 |
| MUC13 | β-hCG | 0.90 |
| CPA1 | AFP | 0.90 |
| CEL | MUC13 | 0.90 |

MUC13 as demonstrated above has an AUC=0.90 for the sample study assessed. AFP has an AUC=0.89 and CPA1 an AUC=0.88.

Combinations show enhanced predictor ability with MUC13+AFP having an AUC=0.94 and MUC13 and CPA1 having an AUC of 0.92

Example 6

CEL levels in maternal serum will be further tested. The levels of CEL will be determined using for example an immunoassay such as an ELISA specific for CEL. The levels of CEL polypeptide in maternal serum of pregnant subjects confirmed for a Down syndrome or trisomy 21-affected fetus will be compared to the levels of CEL polypeptide in maternal serum from women carrying unaffected (e.g. chromosome 21 normal) fetuses. A reproducible difference in maternal serum between affected and unaffected is indicative CEL is a serum biomarker.

Example 7

DPP4 levels in maternal serum will be further tested. The levels of DPP4 will be determined using for example an immunoassay such as an ELISA specific for DPP4. The levels of DPP4 polypeptide in maternal serum of pregnant subjects confirmed for a Down syndrome or trisomy 21-affected fetus will be compared to the levels of DPP4 polypeptide in maternal serum from women carrying unaffected (e.g. chromosome 21 normal) fetuses. A reproducible difference in maternal serum between affected and unaffected is indicative DPP4 is a serum biomarker.

Example 8

CPA1 levels in maternal serum will be further tested. The levels of CPA1 will be determined using for example an immunoassay such as an ELISA specific for CPA1. The levels of CPA1 polypeptide in maternal serum of pregnant subjects confirmed for a Down syndrome or trisomy 21-affected fetus will be compared to the levels of CPA1 polypeptide in maternal serum from women carrying unaffected (e.g. chromosome 21 normal) fetuses. A reproducible difference in maternal serum between affected and unaffected is indicative CPA1 is a serum biomarker.

Example 9

Current screening involves measuring the serum markers pregnancy-associated plasma protein A (PAPP-A) and human chorionic gonadotropin beta (β-hCG) are measured in maternal serum during the first trimester. Alpha fetoprotein (AFP), unconjugated estriol (uE3), and inhibin A are measured in maternal serum during the second trimester. The biomarkers for trisomy 21 described herein will also be used in combination with current screening methods for trisomy 21, including known DS markers and the predictive power e.g. the specificity and sensitivity of the combinations assessed.

For example, maternal serum samples can be obtained from pregnant subjects being tested for a trisomy 21 fetus and from pregnant women who are known to be carrying chromosome 21 normal fetuses. The maternal sera will then be tested for one or more of MUC13, CEL, DPP4, and/or CPA1, as well as for PAPP-A and β-hCG or AFP, uE3, and inhibin A, for example by using a biomarker specific detection agent.

While the present disclosure has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. All sequences (e.g. nucleotide, including RNA and cDNA, and polypeptide sequences) of genes listed in Table 1, 2, and 3, for example referred to by accession number are herein incorporated specifically by reference.

REFERENCES

1. Canfield M A, Honein M A, Yuskiv N, Xing J, Mai C T, Collins J S, et al. National estimates and race/ethnic-specific variation of selected birth defects in the united states, 1999-2001. Birth Defects Res A Clin Mol Teratol 2006; 76:747-56.
2. Antonarakis S E, Lyle R, Dermitzakis E T, Reymond A, Deutsch S. Chromosome 21 and down syndrome: From genomics to pathophysiology. Nat Rev Genet 2004; 5:725-38.
3. Malone F D, Canick J A, Ball R H, Nyberg D A, Comstock C H, Bukowski R, et al. First-trimester or second-trimester screening, or both, for down's syndrome. N Engl J Med 2005; 353:2001-11.
4. Haddow J E, Palomaki G E, Knight G J, Williams J, Pulkkinen A, Canick J A, et al. Prenatal screening for down's syndrome with use of maternal serum markers. N Engl J Med 1992; 327:588-93.
5. Halliday J L, Watson L F, Lumley J, Danks D M, Sheffield L J. New estimates of down syndrome risks at chorionic villus sampling, amniocentesis, and livebirth in women of advanced maternal age from a uniquely defined population. Prenat Diagn 1995; 15:455-65.
6. Cho C K, Shan S J, Winsor E J, Diamandis E P. Proteomics analysis of human amniotic fluid. Mol Cell Proteomics 2007; 6:1406-15.
7. Park S J, Yoon W G, Song J S, Jung H S, Kim C J, Oh S Y, et al. Proteome analysis of human amnion and amniotic fluid by two-dimensional electrophoresis and matrix-assisted laser desorption/ionization time-of-flight mass spectrometry. Proteomics 2006; 6:349-63.
8. Gravett M G, Novy M J, Rosenfeld R G, Reddy A P, Jacob T, Turner M, et al. Diagnosis of intra-amniotic infection by proteomic profiling and identification of novel biomarkers. Jama 2004; 292:462-9.
9. Cho C K, Smith C R, Diamandis E P. Amniotic fluid proteome analysis from down syndrome pregnancies for biomarker discovery. J Proteome Res 2010; 9:3574-82.
10. Perluigi M, di Domenico F, Fiorini A, Cocciolo A, Giorgi A, Foppoli C, et al. Oxidative stress occurs early in down syndrome pregnancy: A redox proteomics analysis of amniotic fluid. Proteomics Clin Appl 2011; 5:167-78.
11. Cheng P J, Wang T H, Huang S Y, Kao C C, Lu J H, Hsiao C H, Shaw S W. Differential proteomics analysis of amniotic fluid in pregnancies of increased nuchal translucency with normal karyotype. Prenat Diagn 2011; 31:274-81.
12. Whiteaker J R, Zhao L, Abbatiello S E, Burgess M, Kuhn E, Lin C, et al. Evaluation of large scale quantitative proteomic assay development using peptide affinity-based mass spectrometry. Mol Cell Proteomics 2011: e-pub ahead of print.
13. Drabovich A P, Diamandis E P. Combinatorial peptide libraries facilitate development of multiple reaction monitoring assays for low-abundance proteins. J Proteome Res 2010; 9:1236-45.
14. Cho C K, Diamandis E P. Application of proteomics to prenatal screening and diagnosis for aneuploidies. Clin Chem Lab Med 2011; 49:33-41.
15. Anderson N L, Anderson N G, Haines L R, Hardie D B, Olafson R W, Pearson T W. Mass spectrometric quantitation of peptides and proteins using stable isotope standards and capture by anti-peptide antibodies (siscapa). J Proteome Res 2004; 3:235-44.
16. Soini Y, Satta J, Maatta M, Autio-Harmainen H. Expression of mmp2, mmp9, mt1-mmp, timp1, and timp2 mrna in valvular lesions of the heart. J Pathol 2001; 194:225-31.
17. Brown D L, Hibbs M S, Kearney M, Loushin C, Isner J M. Identification of 92-kd gelatinase in human coronary atherosclerotic lesions. Association of active enzyme synthesis with unstable angina. Circulation 1995; 91:2125-31.
18. Yang Z, Strickland D K, Bornstein P. Extracellular matrix metalloproteinase 2 levels are regulated by the low density lipoprotein-related scavenger receptor and thrombospondin 2. J Biol Chem 2001; 276:8403-8.
16. Roher A E, Kasunic T C, Woods A S, Cotter R J, Ball M J, Fridman R. Proteolysis of a beta peptide from alzheimer disease brain by gelatinase a. Biochem Biophys Res Commun 1994; 205:1755-61.
19. Yankner B A, Lu T. Amyloid beta-protein toxicity and the pathogenesis of alzheimer disease. J Biol Chem 2009; 284:4755-9.
20. Horstmann S, Budig L, Gardner H, Koziol J, Deuschle M, Schilling C, Wagner S. Matrix metalloproteinases in peripheral blood and cerebrospinal fluid in patients with alzheimer's disease. Int Psychogeriatr; 22:966-72.
21. Bellini C, Rutigliani M, Boccardo F M, Bonioli E, Campisi C, Grillo F, et al. Nuchal translucency and lymphatic system maldevelopment. J Perinat Med 2009; 37:673-6.
22. Shin J W, Jurisic G, Detmar M. Lymphatic-specific expression of dipeptidyl peptidase iv and its dual role in lymphatic endothelial function. Exp Cell Res 2008; 314: 3048-56.
23. Ikushima H, Munakata Y, Ishii T, Iwata S, Terashima M, Tanaka H, et al. Internalization of cd26 by mannose 6-phosphate/insulin-like growth factor ii receptor contributes to t cell activation. Proc Natl Acad Sci USA 2000; 97:8439-44.
24. Kodvawala A, Ghering A B, Davidson W S, Hui D Y. Carboxyl ester lipase expression in macrophages increases cholesteryl ester accumulation and promotes atherosclerosis. J Biol Chem 2005; 280:38592-8.
25. Bocconi L, Nava S, Fogliani R, Nicolini U. Trisomy 21 is associated with hypercholesterolemia during intrauterine life. Am J Obstet Gynecol 1997; 176:540-3.
26. Prasher V P, Airuehia E, Patel A, Haque M S. Total serum cholesterol levels and alzheimer's dementia in patients with down syndrome. Int J Geriatr Psychiatry 2008; 23:937-42.
27. Williams S J, Wreschner D H, Tran M, Eyre H J, Sutherland G R, McGuckin M A. Muc13, a novel human cell surface mucin expressed by epithelial and hemopoietic cells. J Biol Chem 2001; 276:18327-36.
28. Chauhan S C, Vannatta K, Ebeling M C, Vinayek N, Watanabe A, Pandey K K, et al. Expression and functions of transmembrane mucin muc13 in ovarian cancer. Cancer Res 2009; 69:765-74.
29. Walsh M D, Young J P, Leggett B A, Williams S H, Jass J R, McGuckin M A. The muc13 cell surface mucin is highly expressed by human colorectal carcinomas. Hum Pathol 2007; 38:883-92.
30. Moehle C, Ackermann N, Langmann T, Aslanidis C, Kel A, Kel-Margoulis O, et al. Aberrant intestinal expression and allelic variants of mucin genes associated with inflammatory bowel disease. J Mol Med 2006; 84:1055-66.
31. Werner M, Faser C, Silverberg M. Clinical utility and validation of emerging biochemical markers for mammary adenocarcinoma. Clin Chem 1993; 39:2386-2396.
32. Togami S, Nomoto M, Higashi M, Goto M, Yonezawa S, Tsuji T, Batra S K, Douchi T. Expression of mucin antigens (MUC1 and MUC16) as a prognostic factor for mucinous adenocarcinoma of the uterine cervix. Journal of Obstet Gynecol Res 2010; 36:588-597.

33. Pinheiro S P, Hankinson S E, Tworoger S S, Rosner B A, McKolanis J R, Finn O J, Cramer D W. (2010) Anti-MUC1 antibodies and ovarian cancer risk: prospective data from the Nurses' Health Studies. Cancer Epidemiol Biomark Prev 2010; 19:1595-601.
34. Cohen, E. D.; Ihide-Stansbury, K.; Lu, M. M.; Panettieri, R. A.; Jones, P. L.; Morrisey, E. E. Wnt signaling regulates smooth muscle precursor development in the mouse lung via a tenascin C/PDGFR pathway. J. Clin. Invest. 2009, 119 (9), 2538-49.
35. Imanaka-Yoshida, K.; Matsumoto, K.; Hara, M.; Sakakura, T.; Yoshida, T. The dynamic expression of tenascin-C and tenascin-X during early heart development in the mouse. Differentiation 2003, 71 (4-5), 291-8.
36. Ishii, K.; Imanaka-Yoshida, K.; Yoshida, T.; Sugimura, Y. Role of stromal tenascin-C in mouse prostatic development and epithelial cell differentiation. Dev. Biol. 2008, 324 (2), 310-9.
37. Papadopoulos, N.; Simopoulos, C.; Sigalas, J.; Kotini, A.; Cheva, A.; Tamiolakis, D. Induction of hepatic hematopoiesis with tenascin-C expression during the second trimester of development. Eur. J. Obstet. Gynecol. Reprod. Biol. 2004, 113 (1), 56-60.
38. Camacho, C.; Coulouris, G.; Avagyan, V.; Ma, N.; Papadopoulos, J.; Bealer, K.; Madden, T. L., BLAST+: architecture and applications. *BMC Bioinformatics* 2009, 10, 421.
39. MacLean, B.; Tomazela, D. M.; Shulman, N.; Chambers, M.; Finney, G. L.; Frewen, B.; Kern, R.; Tabb, D. L.; Liebler, D. C.; MacCoss, M. J., Skyline: an open source document editor for creating and analyzing targeted proteomics experiments. *Bioinformatics* 2010, 26, 966-8.
40. Spencer, K.; Muller, F.; Aitken, D. A., Biochemical markers of trisomy 21 in amniotic fluid. *Prenat. Diagn.* 1997, 17, 31-7.
41. Maher, D. M.; Gupta, B. K.; Nagata, S.; Jaggi, M.; Chauhan, S. C., Mucin 13: structure, function, and potential roles in cancer pathogenesis. *Mol. Cancer Res.* 2011, 9, 531-7.
42. Hui, D. Y.; Hayakawa, K.; Oizumi, J., Lipoamidase activity in normal and mutagenized pancreatic cholesterol esterase (bile salt-stimulated lipase). *Biochem. J.* 1993, 291, 65-9.

The invention claimed is:

1. An assay comprising:
   a) measuring or quantifying the polypeptide level of at least one biomarker selected from mucin 13 (MUC13), bile salt-activated lipase (CEL), dipeptidyl peptidase 4 (DPP4) and carboxypeptidase A1 (CPA1) polypeptides in a test blood sample or fraction thereof and/or amniotic fluid sample from a pregnant subject; and
   b) comparing the measured or quantified level of the at least one biomarker with a corresponding reference biomarker polypeptide level, and if the level of MUC13, CEL, DPP4, and/or compared to the reference biomarker polypeptide level, identifying the subject as having an increased probability of trisomy 21 in the fetus.

2. The assay of claim 1, wherein the test blood sample or fraction thereof and/or amniotic fluid sample is a sample from the pregnant subject in the first trimester.

3. The assay of claim 1, wherein the at least one biomarker comprises:
   a) MUC13;
   b) MUC13 and CPA1; or
   c) MUC13 and CEL.

4. The assay of claim 1, further comprising measuring or quantifying the level of at least one biomarker selected from pregnancy-associated plasma protein A (PAPP-A), human chorionic gonadotropin beta (β-hCG), Alpha fetoprotein (AFP), unconjugated estriol (uE3) and inhibin A polypeptides in a test blood sample or fraction thereof and/or amniotic fluid sample.

5. The assay of claim 4, wherein the at least one biomarker comprises:
   a) MUC13 and AFP;
   b) MUC13 and β-hCG;
   c) MUC13 and PAPP-A;
   d) MUC13 and uE3; or
   e) MUC13 and inhibin A.

6. The assay of claim 1, wherein the assay is an immunoassay and/or a mass spectrometry assay.

7. The assay of claim 6, wherein the immunoassay is selected from Western blot, ELISA, sandwich ELISA, immunoprecipitation, immunohistochemistry, immunofluorescence, radioimmunoassay, dot blotting, and FACS.

8. A method for screening for an increased risk of trisomy 21 in a fetus the method comprising:
   a) obtaining a test blood sample or fraction thereof and/or amniotic fluid sample from a pregnant subject,
   b) measuring or quantifying the polypeptide level of at least one biomarker selected from mucin 13 (MUC13), bile salt-activated lipase (CEL), and carboxypeptidase A1 (CPA1) in the test blood sample or fraction thereof and/or amniotic fluid sample from the pregnant subject,
   c) comparing the measured or quantified amount of the at least one biomarker with a corresponding reference biomarker polypeptide level, and if the polypeptide level of MUC13, CEL, and/or CPA1 polypeptide is decreased in the test blood sample or fraction thereof and/or amniotic fluid sample compared to the reference biomarker polypeptide level identifying the subject as having an increased probability of trisomy 21 in the fetus.

9. The method of claim 1, wherein the test blood sample or fraction thereof and/or amniotic fluid sample is a sample from the pregnant subject in the first trimester.

10. The method of claim 1, wherein the at least one biomarker comprises:
    a) MUC13;
    b) MUC13 and CPA1; or
    c) MUC13 and CEL.

11. The method of claim 1, wherein the blond fraction plasma or serum.

12. The method of claim 11, wherein the at least one biomarker is MUC13.

13. The method of claim 1, wherein the method is performed on a test blood sample or fraction thereof and/or amniotic fluid sample from the pregnant subject in the first trimester, and the method is repeated on a second blood sample or fraction thereof and/or amniotic fluid sample from the pregnant subject in the second trimester.

14. The method of claim 1, further comprising measuring or quantifying the polypeptide level of at least one biomarker selected from pregnancy-associated plasma protein A (PAPP-A), human chorionic gonadotropin beta (β-hCG), Alpha fetoprotein (AFP), unconjugated estriol (uE3), and inhibin A in a test blood sample or fraction thereof and/or amniotic fluid sample.

15. The method of claim 14, wherein the at least one biomarker comprises:
    a) MUC13 and AFP;
    b) MUC13 and β-hCG;
    c) MUC13 and PAPP-A;
    d) MUC13 and uE3; or
    e) MUC13 and inhibin A.

16. The method of claim 1, wherein measuring or quantifying the polypeptide level of the at least one biomarker comprises an immunoassay and/or mass spectrometric methods.

17. The method of claim 16, wherein the immunoassay is selected from Western blot, ELISA, sandwich ELISA, immunoprecipitation, immunohistochemistry, immunofluorescence, radioimmunoassay, dot blotting, and FACS.

* * * * *

UNITED STATES PATENT AND TRADEMARK OFFICE
CERTIFICATE OF CORRECTION

PATENT NO. : 8,574,860 B2  
APPLICATION NO. : 13/467661  
DATED : November 5, 2013  
INVENTOR(S) : Eleftherios P. Diamandis et al.

Page 1 of 1

It is certified that error appears in the above-identified patent and that said Letters Patent is hereby corrected as shown below:

In the Claims

Claim 1, Column 52, line 57, "CEL, DPP4, and/or compared to the reference biomar-..." should read -- CEL, DPP4, and/or CPA1 polypeptide is decreased in the test blood sample or fraction thereof and/or amniotic fluid sample compared to the reference biomar-... --.

Claim 9, Column 53, line 38, "The method of claim 1, wherein the test blood sample or..." should read -- The method of claim 8, wherein the test blood sample or... --.

Claim 10, Column 54, line 1, "The method of claim 1, wherein..." should read -- The method of claim 8, wherein... --.

Claim 11, Column 54, lines 6 and 7, "The method of claim 1 wherein the blond fraction plasma or serum." should read -- The method of claim 8 wherein the blood fraction is plasma or serum. --.

Claim 11, Column 54, line 16, "The method of claim 1, further comprising measuring..." should read -- The method of claim 8, further comprising measuring... --.

Claim 14, Column 54, line 20, "protein (AFP), unconjugated estriol (uE3), and inhibin A in a..." should read -- protein (AFP), unconjugated estriol (uE3) and inhibin A in a... --.

Claim 16, Column 54, line 30, "The method of claim 1, wherein..." should read -- The method of claim 8, wherein... --.

Signed and Sealed this  
Eighteenth Day of February, 2014

Michelle K. Lee  
*Deputy Director of the United States Patent and Trademark Office*